(12) United States Patent
Fricke et al.

(10) Patent No.: US 12,727,801 B2
(45) Date of Patent: Sep. 8, 2026

(54) ADDITIVE MIXING FOR BLOOD SAMPLE COLLECTION

(71) Applicant: Becton, Dickinson and Company, Franklin Lakes, NJ (US)

(72) Inventors: Alex F. Fricke, Cedar Knolls, NJ (US); Anthony V. Torris, Mercer Island, WA (US); Kishore K. Bokka Srinivasa Rao, Ridgewood, NJ (US); Scott Wentzell, Suffern, NY (US); Vlad Yakhnich, Park Ridge, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 986 days.

(21) Appl. No.: 17/966,108

(22) Filed: Oct. 14, 2022

(65) Prior Publication Data

US 2023/0122154 A1 Apr. 20, 2023

Related U.S. Application Data

(60) Provisional application No. 63/256,155, filed on Oct. 15, 2021.

(51) Int. Cl.
*A61B 5/00* (2006.01)
*A61B 5/15* (2006.01)

(52) U.S. Cl.
CPC .. *A61B 5/150755* (2013.01); *A61B 5/150206* (2013.01); *A61B 5/150267* (2013.01); *A61B 5/150748* (2013.01)

(58) Field of Classification Search
CPC ........ A61B 5/150755; A61B 5/150206; A61B 5/150267; A61B 5/150748;
(Continued)

(56) References Cited

U.S. PATENT DOCUMENTS 4,214,874 A 7/1980 White
4,646,753 A 3/1987 Nugent
(Continued)

FOREIGN PATENT DOCUMENTS

DE 2850548 A1 6/1980
DE 10315396 A1 10/2004
(Continued)

*Primary Examiner* — May A Abouelela
(74) *Attorney, Agent, or Firm* — The Webb Law Firm

(57) ABSTRACT

A sample collection container configured to be removably mounted to a blood collection device includes: a housing having a flow channel extending through the housing having an inlet and an outlet and a container body removably connected to the housing. The container body includes an open top, a closed bottom, and an interior wall extending between the top and the bottom defining a collection cavity. When the housing is connected to the container body, the outlet of the flow channel is in fluid communication with the collection cavity. The sample collection container also includes at least one additive dispersing object positioned to be contacted by blood flowing from the blood collection device through the flow channel and/or into the collection cavity. The at least one additive dispersing object includes an additive composition to be mixed with the blood passing along the flow channel and into the collection cavity.

29 Claims, 22 Drawing Sheets

(58) Field of Classification Search
CPC ........ A61B 5/150068; A61B 5/150251; A61B 5/15113; A61B 5/15117; A61B 5/15194; A61B 5/150305; A61B 5/150343; A61B 5/150022; A61B 5/1519; A61B 5/157; B01L 2200/16; B01L 2400/0406; B01L 3/5021
See application file for complete search history.

(56) References Cited

U.S. PATENT DOCUMENTS 4,690,153 A 9/1987 Losada et al.
4,805,635 A 2/1989 Korf et al.
5,181,523 A 1/1993 Wendelborn
5,485,856 A 1/1996 Buckland
5,795,061 A 8/1998 Perlman
6,398,758 B1 6/2002 Jacobsen et al.
6,679,852 B1 1/2004 Schmelzeisen-Redeker et al.
8,372,015 B2 2/2013 Escutia et al.
9,192,749 B2 * 11/2015 Trautman ........... A61B 5/15117
9,380,975 B2 7/2016 Karbowniczek et al.
9,566,027 B2 2/2017 Tamir
9,636,051 B2 5/2017 Emery et al.
9,833,183 B2 12/2017 Escutia et al.
9,849,251 B2 12/2017 Crawford et al.
10,499,840 B2 12/2019 Bartfeld et al.
2006/0052809 A1 3/2006 Karbowniczek et al.
2006/0057033 A1 * 3/2006 Goldenberg .......... B01L 3/5082 422/419
2006/0212020 A1 * 9/2006 Rainen ................... A01N 1/126 604/403
2007/0083131 A1 4/2007 Escutia et al.
2009/0112125 A1 4/2009 Tamir
2009/0155838 A1 * 6/2009 Hale ....................... B01L 3/505 435/7.1
2009/0198152 A1 8/2009 Kim
2009/0259145 A1 10/2009 Bartfeld et al.
2010/0099074 A1 * 4/2010 Nolan ................... F16K 99/003 435/307.1
2011/0118568 A1 5/2011 Sei
2011/0124984 A1 5/2011 Rostaing
2013/0209985 A1 * 8/2013 Hoke .................... B01L 3/5021 435/307.1
2014/0017693 A1 * 1/2014 Mao ..................... G01N 33/521 435/6.12
2014/0272925 A1 * 9/2014 Menon .................. B01L 3/5021 435/307.1
2015/0351676 A1 12/2015 Faurie et al.
2016/0174888 A1 6/2016 Berthier et al.
2017/0067803 A1 * 3/2017 Jackson ............... C12Q 1/6806
2019/0086380 A1 * 3/2019 Harding ................ B01L 3/5029
2019/0120727 A1 * 4/2019 Harding ................... G01N 1/02
2019/0216380 A1 7/2019 Ivosevic et al.
2019/0223772 A1 7/2019 Bokka Srinivasa Rao et al.
2019/0357829 A1 * 11/2019 Weinberg ......... A61B 5/150282
2020/0147615 A1 * 5/2020 Huang ................... G01N 15/14
2020/0188910 A1 * 6/2020 Gumbrecht ...... G01N 33/54393
2020/0238247 A1 * 7/2020 Kraft ..................... C08F 220/56
2020/0241020 A1 * 7/2020 Oshinski ................... B01L 3/52
2020/0261914 A1 * 8/2020 Ririe ...................... C12N 15/10
2020/0359953 A1 11/2020 Edelhauser et al.
2021/0161446 A1 * 6/2021 Ivosevic .......... A61B 5/150099
2021/0186393 A1 6/2021 McHale et al.
2021/0196164 A1 7/2021 Tosevic
2021/0219890 A1 * 7/2021 Ivosevic ............ A61B 5/15074
2022/0386913 A1 * 12/2022 Komai .................. B01L 3/5021
2023/0050815 A1 * 2/2023 Setoguchi ........ A61B 5/150206
2023/0090675 A1 * 3/2023 Komai ................. G01N 33/491 435/287.1
2023/0133549 A1 * 5/2023 Turzi ...................... A61P 31/14 435/372
2023/0400457 A1 * 12/2023 Medkova .............. B01L 3/0275
2023/0405577 A1 * 12/2023 Pugia ...................... B01L 3/502

FOREIGN PATENT DOCUMENTS

EP 0224650 A2 10/1987
EP 1157660 A1 11/2001
EP 2184012 A1 12/2010
GB 2183159 A 6/1987
GB 2409411 A 6/2005
JP H1024027 A 1/1998
JP 2002219115 A 8/2002
RU 2013158818 A 7/2015
WO 02100254 A2 12/2002
WO 2004064637 A1 8/2004
WO 2008027319 A2 3/2008
WO 2009081405 A2 7/2009
WO 2009145920 A1 12/2009
WO 2015191853 A1 12/2015
WO 2016060795 A1 4/2016
WO 2019165407 A1 8/2019
WO 2020167746 A1 8/2020

* cited by examiner 110
150
152
140
162
142
156
158
130
132
134
112
116
114

110
150
152
162
140
156
158
130
132
134
112
116
114

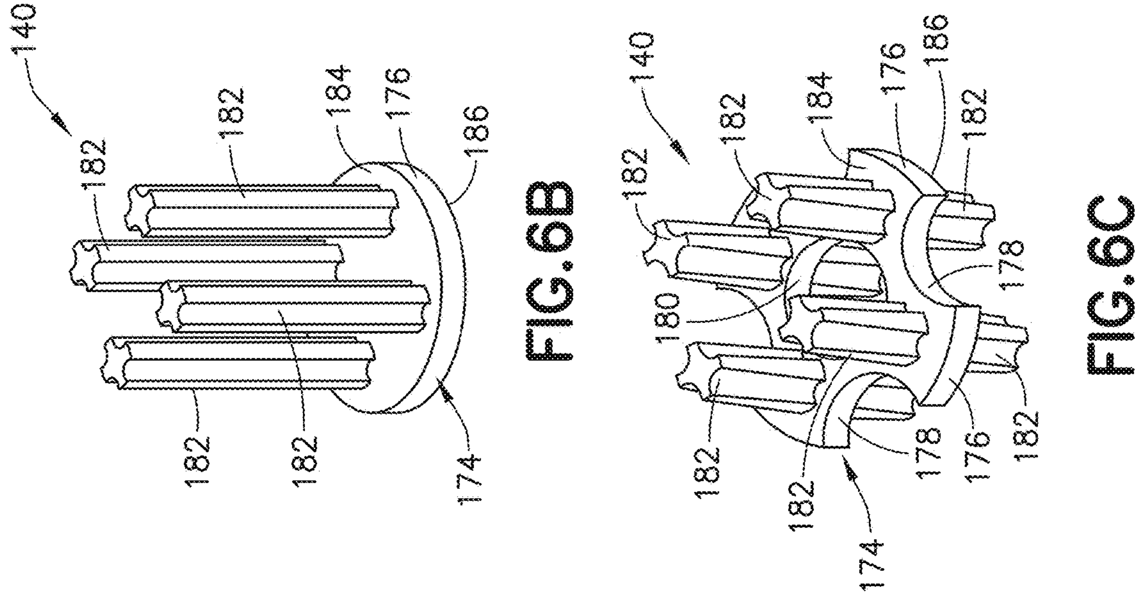
FIG.6B
FIG.6C
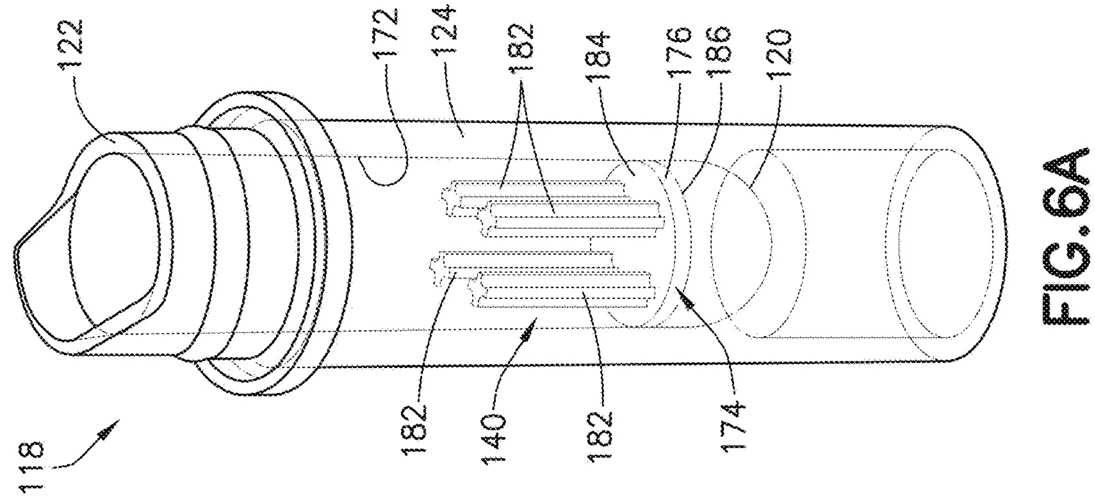
FIG.6A

ADDITIVE MIXING FOR BLOOD SAMPLE COLLECTION

CROSS-REFERENCE TO RELATED APPLICATION

The present application claims priority to U.S. Provisional Application Ser. No. 63/256,155, entitled "Additive Mixing for Blood Sample Collection", filed Oct. 15, 2021, the entire disclosure of which is hereby incorporated by reference in its entirety.

BACKGROUND OF THE INVENTION

Field of the Invention

The present disclosure relates generally to collection containers for containing a biological sample, such as a blood sample. More particularly, the present disclosure relates to a sample collection container configured to connect to and receive a blood sample from a blood collection device, such as a finger-based capillary blood collection device, including features for passively or actively mixing the collected blood sample with an additive composition, such as an anticoagulant.

Description of Related Art

Devices for obtaining and collecting biological samples, such as blood samples, are commonly used in the medical industry. One type of blood collection that is commonly done in the medical field is capillary blood collection, which is often done to collect blood samples for testing. Certain diseases, such as diabetes, require that a patient's blood be tested on a regular basis to monitor, for example, the patient's blood sugar levels. Additionally, test kits, such as cholesterol test kits, often require a blood sample for analysis. The blood collection procedure usually involves pricking a finger or other suitable body part in order to obtain the blood sample. Typically, the amount of blood needed for such tests is relatively small and a small puncture wound or incision normally provides a sufficient amount of blood for these tests. Various types of lancet devices have been developed, which are used for puncturing the skin of a patient, to obtain a capillary blood sample from the patient.

Many different types of lancet devices are commercially available to hospitals, clinics, doctors' offices, and the like, as well as to individual consumers. Such devices typically include a sharp-pointed member, such as a needle, or a sharp-edged member, such as a blade, that is used to make a quick puncture wound or incision in the patient's skin in order to provide a small outflow of blood. In order to simplify capillary blood collection, lancet devices have evolved into automatic devices that puncture or cut the skin of the patient upon actuation of a triggering mechanism. In some devices, the needle or blade is kept in a standby position until it is triggered by the user. Upon triggering, the needle or blade punctures or cuts the skin of the patient, for example, on the finger. Often, a spring is incorporated into the device to provide the "automatic" force necessary to puncture or cut the skin of the patient. One type of contact activated lancet device that features automatic ejection and retraction of the puncturing or cutting element from and into the device is U.S. Pat. No. 9,380,975, entitled "Contact activated lancet device," which is incorporated herein by reference in its entirety.

Use of lancet devices for capillary blood collection can be complex requiring a high skill level for the healthcare worker performing the blood collection procedure. The multi-step nature of the capillary blood collection process can introduce several variables that may cause sample quality issues, such as hemolysis, inadequate sample stabilization, and micro-clots. In particular, micro-clots can occur when the blood sample is not adequately mixed with the anticoagulant either as the blood sample is being introduced into the collection container or, after the sample is in the container, by applying an external mixing force to the container. Due to the possibility that inadequate mixing may damage or destroy a collected sample, there is a need for devices and methods that improve or encourage complete mixing. In particular, the devices and methods should quickly and completely disperse the additive composition, such as an anticoagulant, through a blood sample, thereby substantially reducing the risk that micro-clots will form in the collected blood sample.

SUMMARY OF THE INVENTION

According to an aspect of the disclosure, a sample collection container configured to be removably mounted to a blood collection device includes: a housing having a first end, a second end, a flow channel having an inlet and an outlet extending at least partially between the first end and the second end of the housing and a container body removably connected to the second end of the housing. The container body includes an open top, a closed bottom, and an interior wall extending between the top and the bottom. The interior wall defines a collection cavity. When the housing is connected to the container body, the outlet of the flow channel is in fluid communication with the collection cavity. The sample collection container also includes at least one additive dispersing object positioned to be contacted by blood flowing from the blood collection device through the flow channel and/or into the collection cavity. The at least one additive dispersing object includes an additive composition to be mixed with the blood passing along the flow channel and into the collection cavity.

According to another aspect of the disclosure, a blood collection assembly includes: a finger holder having a finger receiving portion and an actuation portion; and a sample collection container configured to be removably mounted to the finger holder. The sample collection container includes: a housing having a first end removably connectable to the finger holder, a second end, a flow channel having an inlet and an outlet extending at least partially between the first end and the second end of the housing, and at least one flow directing protrusion adjacent the inlet for directing blood from the blood collection device into the flow channel; and a container body removably connected to the second end of the housing. The container body includes an open top, a lower portion having a closed bottom, and an interior wall extending between the top and the bottom. The interior wall defines a collection cavity. When the housing is connected to the container body, the outlet of the flow channel is in fluid communication with the collection cavity. The sample collection container also includes at least one additive dispersing object positioned to be contacted by blood flowing from the blood collection assembly through the flow channel and/or into the collection cavity. The at least one additive dispersing object includes an additive composition to be mixed with the blood passing along the flow channel and into the collection cavity.

According to another aspect of the disclosure, a sample collection container configured to be removably mounted to a blood collection device includes a container body removably connected to the blood collection device which defines a collection cavity. The container body includes an open top, a closed bottom, and an interior wall extending between the top and the bottom, and a cap removably connectable over the container body. The cap includes an open top, an open bottom, and a cap sidewall between the top and the bottom. An interface between an inner surface of the interior wall of the container body and an inner surface of the cap sidewall is flush.

According to another aspect of the disclosure, a reverse centrifugation method includes: collecting a blood sample within any of the previously described sample collection containers; sealing the sample collection container; inserting the sample collection container into a receptacle of a centrifuge in an inverted orientation, with the cap of the container inserted into the receptacle; and activating the centrifuge.

Non-limiting illustrative examples of embodiments of the present disclosure will now be described in the following numbered clauses:

Clause 1: A sample collection container configured to be removably mounted to a blood collection device, the sample collection container comprising: a housing comprising a first end, a second end, a flow channel having an inlet and an outlet extending at least partially between the first end and the second end of the housing; a container body removably connected to the second end of the housing comprising an open top, a closed bottom, and an interior wall extending between the top and the bottom, which define a collection cavity, wherein, when the housing is connected to the container body, the outlet of the flow channel is in fluid communication with the collection cavity; and at least one additive dispersing object positioned to be contacted by blood flowing from the blood collection device through the flow channel and/or into the collection cavity, the at least one additive dispersing object comprising an additive composition to be mixed with the blood passing along the flow channel and into the collection cavity.

Clause 2: The sample collection container of clause 1, wherein the housing further comprises at least one flow directing protrusion adjacent the inlet for directing blood from the blood collection device into the flow channel.

Clause 3: The sample collection container of clause 2, wherein the at least one flow directing protrusion is configured to provide a fluid attachment point for blood to attach to, thereby controlling the flow of blood from a skin surface of a patient's finger to the flow channel of the housing.

Clause 4: The sample collection container of clause 3, wherein the blood is pulled from a surface of the at least one flow directing protrusion through the flow channel to the outlet of the flow channel via capillary action.

Clause 5: The sample collection container of clause 2 or clause 3, wherein the at least one flow directing protrusion comprises an attachment pillar.

Clause 6: The sample collection container of any of clauses 1-5, wherein the bottom of the container body comprises a sloped bottom that slopes towards a portion of the interior wall of the container body forming a depression sized to receive the at least one additive dispersing object.

Clause 7: The sample collection container of clause 6, wherein, when the at least one additive dispersing object is received in the depression, the at least one additive dispersing object does not interfere with a probe inserted into the container cavity through the open top of the container body.

Clause 8: The sample collection container of any of clauses 1-7, wherein the container cavity comprises a volume of about 50 μL to about 500 μL.

Clause 9: The sample collection container of any of clauses 1-8, wherein the additive composition comprises a sample stabilizing composition and/or a composition that preserves a specific element of blood, such as RNA or a protein analyte.

Clause 10: The sample collection container of any of clauses 1-9, wherein the additive composition comprises a dry anticoagulant, such as Heparin or Ethylenediaminetetraacetic acid (EDTA).

Clause 11: The sample collection container of any of clauses 1-10, wherein the at least one additive dispersing object comprises an open cell foam or a closed cell foam that is impregnated with the additive composition.

Clause 12: The sample collection container of any of clauses 1-11, wherein the at least one additive dispersing object comprises an open cell foam comprising at least one of melamine or formaldehyde-melamine-sodium bisulfite copolymer.

Clause 13: The sample collection container of clause 12, wherein the open cell foam is a hydrophilic open cell foam.

Clause 14: The sample collection container of any of clauses 1-13, wherein the at least one additive dispersing object is disposed proximate to the inlet of the flow channel of the housing.

Clause 15: The sample collection container of any of clauses 1-14, wherein the at least one additive dispersing object comprises an elongated pillar configured to be mounted over the at least one directing protrusion.

Clause 16: The sample collection container of any of clauses 1-15, wherein the at least one additive dispersing object is adhered to an inner surface of the interior wall of the container body.

Clause 17: The sample collection container of any of clauses 1-16, wherein the at least one additive dispersing object comprises a hollow, tubular foam structure formed by an extrusion process.

Clause 18: The sample collection container of any of clauses 1-17, wherein the at least one additive dispersing object comprises a molded part comprising an exterior surface coated by the additive composition.

Clause 19: The sample collection container of clause 18, wherein the molded part comprises: a disk sized to fit within the collection cavity of the container body to stabilize the molded part within the container cavity in an upright orientation; and at least one post extending from either an upper surface or a lower surface of the disk.

Clause 20: The sample collection container of clause 19, wherein, in the upright orientation, a longitudinal axis of the at least one post is parallel to a longitudinal axis of the container body.

Clause 21: The sample collection container of clause 19 or clause 20, wherein the at least one post comprises a plurality of lower posts extending downwardly from a lower surface of the disk, and wherein the plurality of lower posts comprise radially inwardly angled free ends.

Clause 22: The sample collection container of clause 21, further comprising a ball at least partially retained by the inwardly angled free ends of the lower posts configured to move through the container cavity to agitate blood in the container cavity.

Clause 23: The sample collection container of any of clauses 1-22, further comprising an agitation member, such as a buoyant or heavy ball, disposed in the container cavity and configured to move through the container cavity to agitate blood in the container cavity.

Clause 24: The sample collection container of any of clauses 1-23, further comprising an agitation tool positioned in the collection cavity proximate to the outlet of the flow channel for agitating blood as it is expelled from the flow channel into the container cavity.

Clause 25: The sample collection container of clause 24, wherein the agitation tool comprises a fin or blade extending about a post positioned such that the blood expelled from the flow channel contacts the fin or blade causing the fin or blade to rotate about the post, thereby agitating the blood and mixing the blood with the additive composition.

Clause 26: A blood collection assembly comprising: a finger holder comprising a finger receiving portion and an actuation portion; and a sample collection container configured to be removably mounted to the finger holder, the sample collection container comprising: a housing comprising a first end removably connectable to the finger holder, a second end, a flow channel having an inlet and an outlet extending at least partially between the first end and the second end of the housing, and at least one flow directing protrusion adjacent the inlet for directing blood from the blood collection device into the flow channel; a container body removably connected to the second end of the housing comprising an open top, a lower portion comprising a closed bottom, and an interior wall extending between the top and the bottom, which define a collection cavity, wherein, when the housing is connected to the container body, the outlet of the flow channel is in fluid communication with the collection cavity; and at least one additive dispersing object positioned to be contacted by blood flowing from the blood collection assembly through the flow channel and/or into the collection cavity, the at least one additive dispersing object comprising an additive composition to be mixed with the blood passing along the flow channel and into the collection cavity.

Clause 27: The blood collection assembly of clause 26, wherein the additive composition comprises a sample stabilizing composition and/or a composition that preserves a specific element of blood, such as RNA or a protein analyte.

Clause 28: The blood collection assembly of clause 26 or clause 27, wherein the additive composition comprises a dry anticoagulant, such as Heparin or Ethylenediaminetetraacetic acid (EDTA).

Clause 29: The blood collection assembly of any of clauses 26-28, wherein the at least one additive dispersing object comprises an open cell foam or a closed cell foam that is impregnated with the additive composition.

Clause 30: The blood collection assembly of any of clauses 26-29, wherein the at least one additive dispersing object comprises an open cell foam comprising at least one of melamine or formaldehyde-melamine-sodium bisulfite copolymer.

Clause 31: The blood collection assembly of any of clauses 26-30, further comprising an electronic vibrator mounted to the finger holder that, when activated, agitates a fluid sample contained in the sample collection container.

Clause 32: The blood collection assembly of any of clauses 26-31, further comprising a magnetic stirrer mounted to the finger holder that, when activated, causes a magnetic stirrer rod in the sample collection container to spin, thereby agitating a blood sample in the sample collection container.

Clause 33: A sample collection container configured to be removably mounted to a blood collection device, the collection container comprising: a container body removably connected to the blood collection device which defines a collection cavity, the container body comprising an open top, a closed bottom, and an interior wall extending between the top and the bottom, and a cap removably connectable over the container body, the cap comprising an open top, an open bottom, and a cap sidewall between the top and the bottom, wherein an interface between an inner surface of the interior wall of the container body and an inner surface of the cap sidewall is flush.

Clause 34: The sample collection container of clause 33, wherein the cap comprises a lid that is moveable between an open position, where the lid is separate from the open top of the cap, and a closed position, where the lid covers the open top of the cap, the lid comprising: a lid body; a flexible connection between the lid body and the sidewall of the cap; and a pierceable septum mounted to the lid body that seals the open top when the lid is in the closed position.

Clause 35: The sample collection container of clause 33 of clause 34, wherein the inner surface of the interior wall proximate to the open top of the container body is tapered, such that, when the cap is connected to the container body, the interface between the inner surface of the interior wall and the inner surface of the cap is free from protrusions.

Clause 36: The sample collection container of any of clauses 33-35, further comprising a lubricant applied to the interface between the inner surface of the interior wall of the container body and the inner surface of the sidewall of the cap.

Clause 37: The sample collection container of any of clauses 33-36, further comprising an additive composition on the inner surface of the interior wall of the container body, wherein the additive composition is applied by spray drying.

Clause 38: The sample collection container of any of clauses 33-37, further comprising at least one additive dispersing object comprising an additive composition positioned within the container body, the additive dispersing object comprising a hydrophilic open cell foam.

Clause 39: A reverse centrifugation method comprising: collecting a blood sample within the sample collection container of any of clauses 33-38; sealing the sample collection container; inserting the sample collection container into a receptacle of a centrifuge in an inverted orientation, with the cap of the container inserted into the receptacle; and activating the centrifuge.

Clause 40: The method of clause 39, wherein the receptacle positions the sample collection container at an angle such that, following centrifugation, a single gel layer separates serum from whole blood, and no gel is above the serum.

Clause 41: The method of clause 39 or clause 40, wherein the receptacle positions the sample collection container at an angle such that, following centrifugation, the gel is entirely within the cap of the sample collection container and not in the container body.

Clause 42: The method of any of clauses 39-41, wherein the receptacle of the centrifuge positions the sample collection container at an angle of from about 65 degrees to about 85 degrees relative to an upright position.

BRIEF DESCRIPTION OF THE DRAWINGS

FIG. 6A is a perspective view of another example of a sample collection container, according to an aspect of the present disclosure.

FIGS. 6B and 6C are perspective views of different additive dispersing objects, according to aspects of the present disclosure.

DESCRIPTION OF THE INVENTION

Figure 1A:
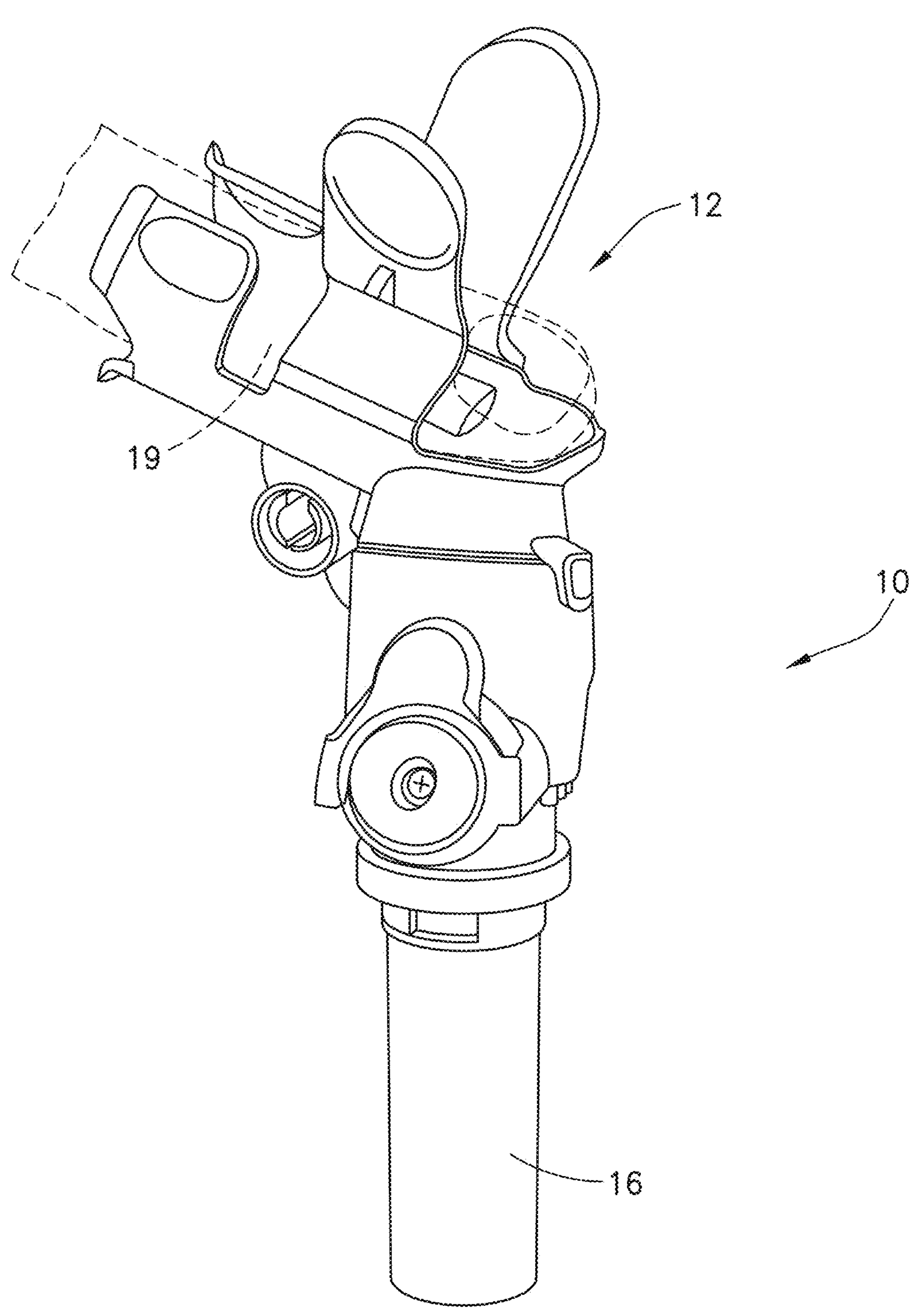
FIG. 1A is a perspective view of a capillary blood collection device for obtaining a blood sample from a patient's finger and a collection container, according to an aspect of the present disclosure.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present disclosure relates to blood collection devices 10 or assemblies configured to collect a capillary blood sample and including a sample collection container 16 for receiving the blood sample. The sample collection container 16 can be configured to perform and/or used for one or more of: passive/auto mixing of a blood sample with an additive composition as the blood sample is being introduced into the sample collection container 16; active mixing achieved by creating turbulent flow in the sample collection container 16 by a tool or other object in the container 16, thereby causing the additive composition to be uniformly mixed into the collected blood sample; and/or for active mixing of the blood sample by an agitation or mixing machine, such as a vortex or centrifuge.

As used herein, the "additive composition" can be a sample stabilizer (i.e., a composition selected to preserve a blood sample and/or to preserve at least a specific element or components of the blood sample). The additive composition can be an anticoagulant, for example, a dry anticoagulant such as Heparin or Ethylenediaminetetraacetic acid (EDTA). In some examples, the additive composition preserves specific elements or components of a blood sample, such as RNA, protein analytes, and/or any other element of the blood sample.

The present disclosure also relates to additive dispersing objects 140 configured to be positioned within or proximate to the sample collection container 16 that contact the blood sample, thereby dispersing the additive composition into the blood sample. As used herein, the "additive dispersing object" can be an object that is coated by, impregnated with, or which otherwise contains the additive composition. The additive dispersing object 140 is configured to be contacted by the blood sample and to disperse the additive composition when in contact with the blood sample. As described in further detail herein, the additive dispersing object 140 can be a porous structure, such as an open cell foam that absorbs the additive composition. The additive dispersing object 140 can also be a denser or more solid structure (i.e., a nonporous structure) with the additive composition coated to an outer surface of the structure. The additive dispersing object 140 can be any convenient shape that fits within or proximate to the sample collection container 16, including, for example, a sphere, ellipsoid, cylinder, ring, donut, cube, polygonal prism, or other regular or irregular shapes. The additive dispersing object 140 can also include strings or threads that are woven together or arranged in a ball or another amalgamation and positioned within the sample collection container 16.

Blood Collection Assembly or Device

Examples of blood collection devices 10 or assemblies that can be used with the various exemplary sample collection containers 16 of the present disclosure are shown in FIGS. 1A-1E. The blood collection devices 10 can be, for example, a self-contained and fully integrated finger-based capillary blood collection device with the ability to lance, collect, and stabilize a high volume capillary blood sample, e.g., up to or above 500 microliters, in the sample collection container 16. The blood collection device 10 or assembly can also be formed from separable components (i.e., a finger cuff, lance, and reservoir) that can be connected and/or used together to obtain a blood sample. Other exemplary capillary blood collection devices and assemblies that can be used with and/or modified to include features of the present disclosure are described, for example, in U.S. Patent Appl. Pub. No. 2019/0216380, entitled "Device for Obtaining a Blood Sample" and PCT Publication No. WO 2020/167746, entitled "Capillary collector with rotatable connection," each of which is incorporated herein by reference in its entirety.

Figure 1B:
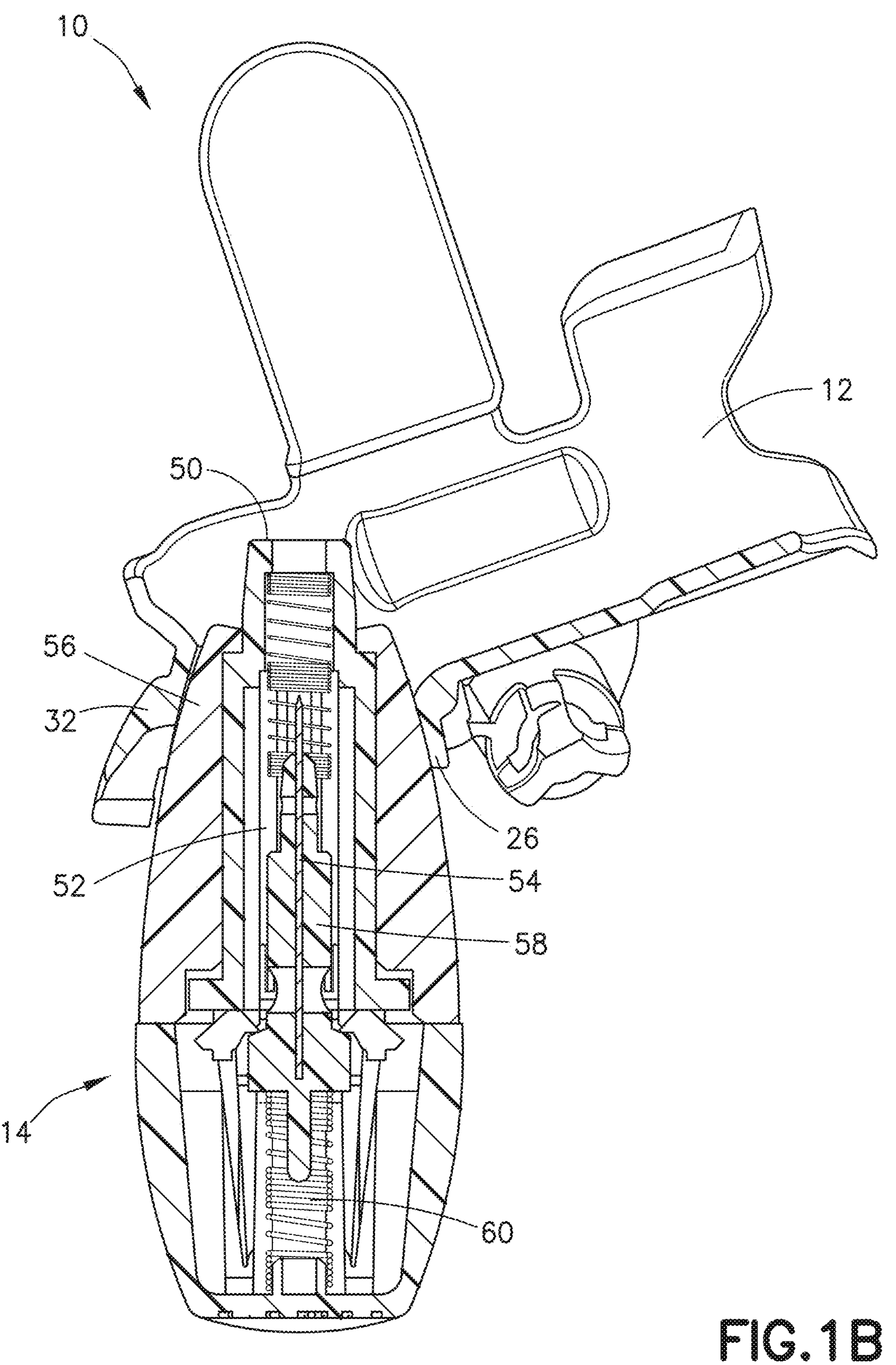
FIG. 1B is a cross-sectional view of a capillary blood collection device and lancet, according to an aspect of the present disclosure.

With reference to FIGS. 1A and 1B, the example blood collection device 10 includes an integrated holder 12, a lancet housing or lancet 14 (shown in FIG. 1B) for puncturing a finger 19 (shown in FIGS. 1D and 1E) of the patient, and the sample collection container 16. In other examples, the blood collection device 10 can be provided as a semi-integrated device 10 including, for example, an integrated lancet housing 14 and collection container 16 that can be connected with a separate holder 12. In other examples, a semi-integrated device 10 may include an integrated lancet housing 14 and collection container 16 connected with a separate holder 12.

Figure 1C:
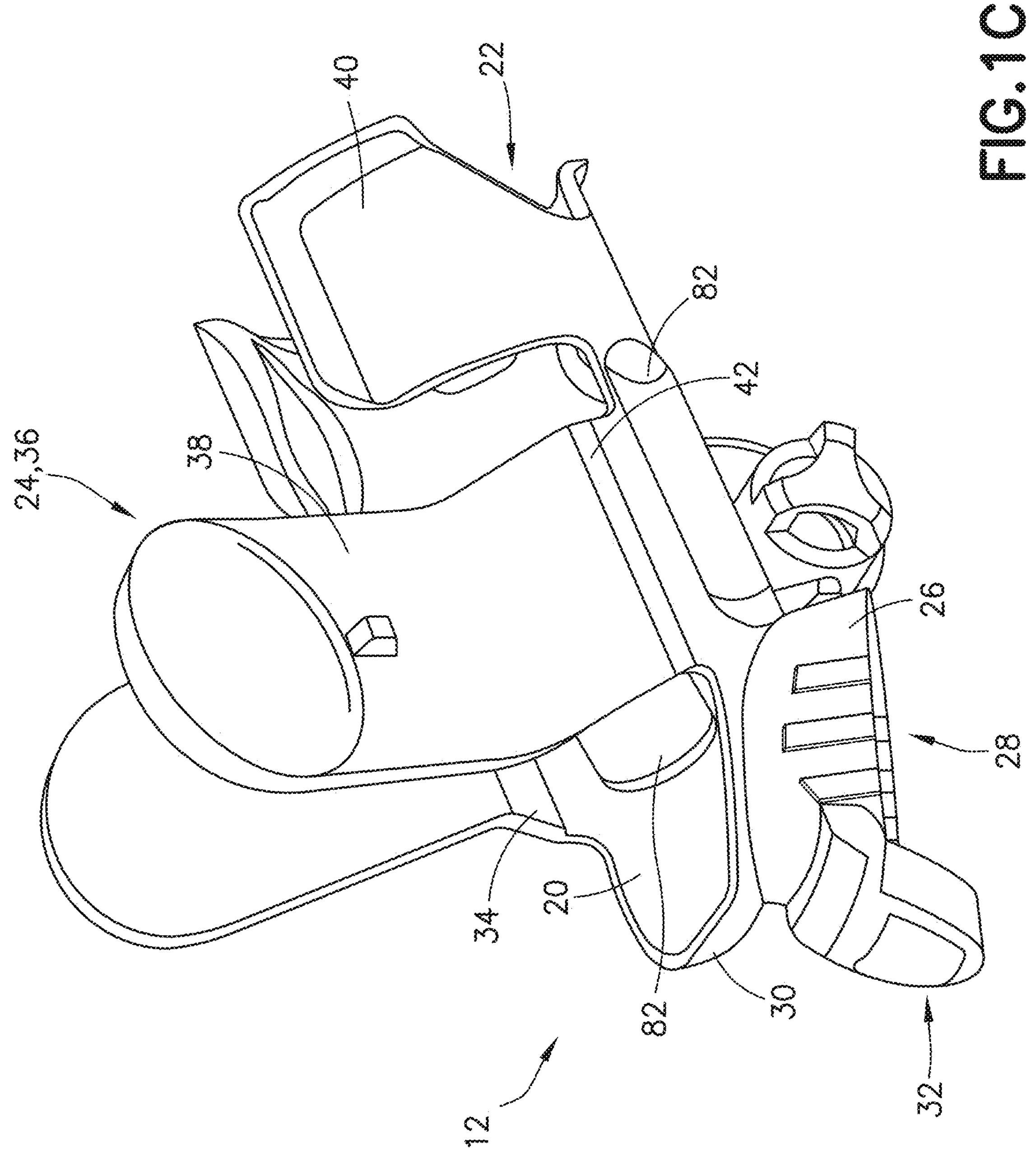
FIG. 1C is a perspective view of a holder of a capillary blood collection device, according to an aspect of the present disclosure.
Figure 1D:
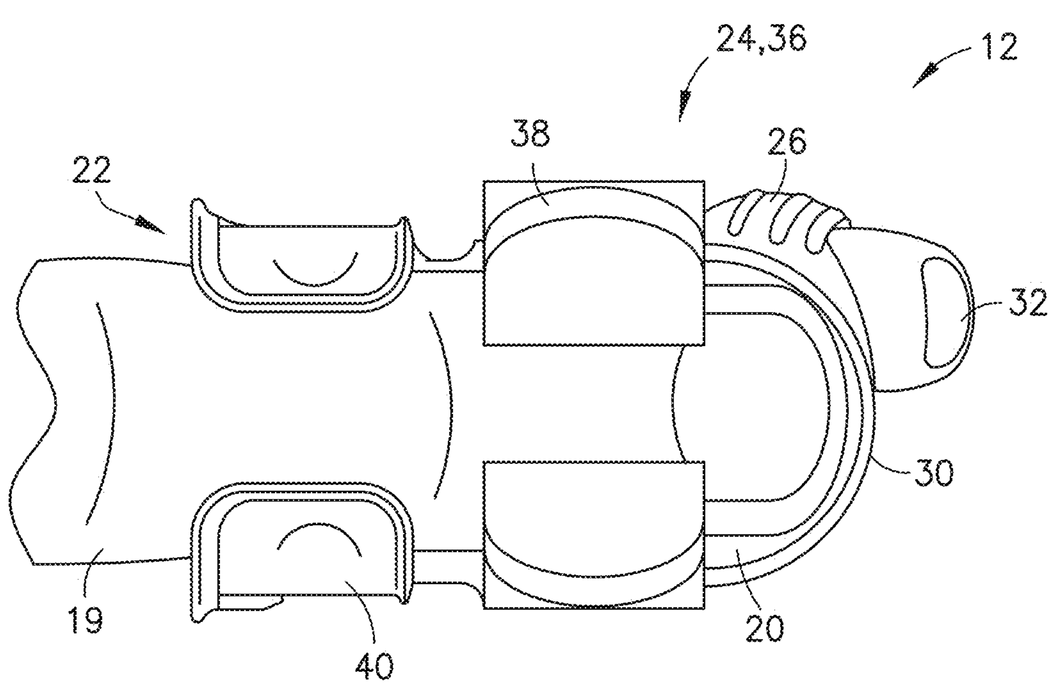
FIG. 1D is a schematic drawing showing a top view of the holder of FIG. 1C connected to a patient's finger for performing a blood collection procedure.
Figure 1E:
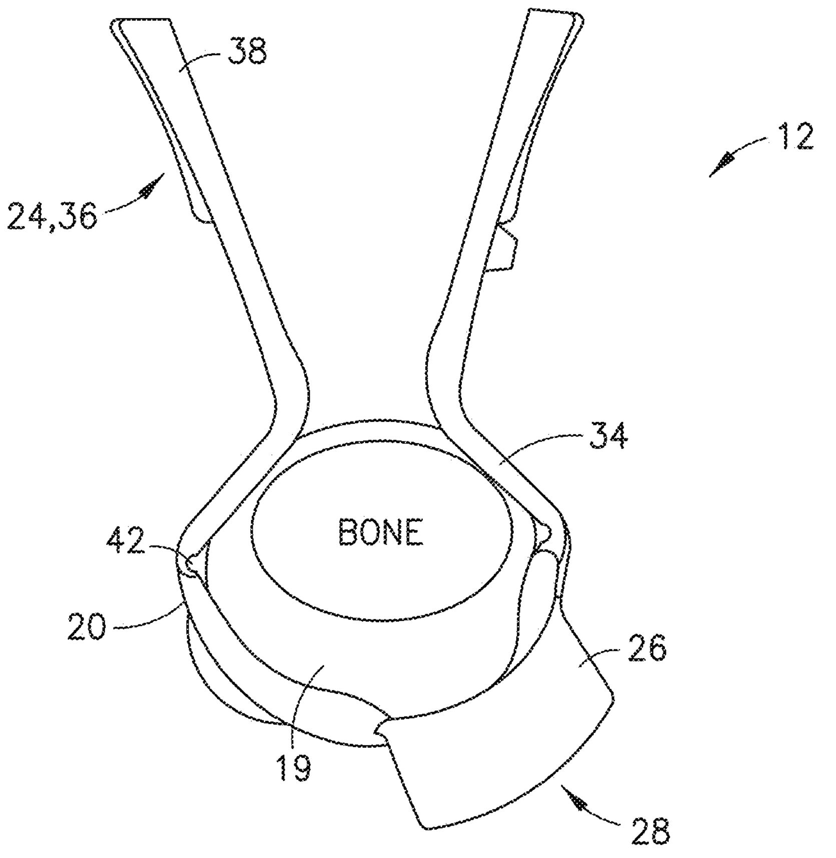
FIG. 1E is another schematic drawing showing a front view of the holder of FIG. 1C connected to the patient's finger.

The holder 12 is configured to receive a sample source, e.g., the finger 19 of a patient, for supplying a biological sample, such as a blood sample. As shown in FIGS. 1C-1E, the holder 12 generally includes a finger receiving portion 20 having a first opening 22, an actuation portion 24, a port 26 having a second opening 28, and a finger end guard 30. In some examples, the finger end guard 30 provides a stop portion for properly aligning and securing the finger 19 within the holder 12. The finger end guard 30 further assists in ensuring the patient's finger 19 is placed at a proper position within the finger receiving portion 20 so that applied pressure to the patient's finger 19 will result in adequate blood flow. The finger end guard 30 can have a curved fingertip rest that ensures the patient's finger 19 stops at an end of the finger receiving portion 20, while permitting the patient's finger nail to clear the end of the finger receiving portion 20. The finger receiving portion 20 permits use of the holder 12 with artificial and natural fingernail styles present in the patient population.

The first opening 22 of the finger receiving portion 20 is configured for receiving the sample source, e.g., the finger 19. The sample source may also include other parts of the body capable of fitting within the first opening 22, such as toes or other extremities. The port 26 is in communication with the finger receiving portion 20. For example, with a finger 19 received within the holder 12, the port 26 is in communication with a portion of the finger 19. The second opening 28 of the port 26 is configured for receiving the lancet housing or lancet 14 (shown in FIG. 1B) and the collection container 16. In some examples, the port 26 further includes a locking portion 32 for securely receiving the lancet housing or lancet 14 and the collection container 16 within the port 26.

The actuation portion 24 of the device 10 is transitionable between a first position, in which the holder 12 defines a first diameter, and a second position, in which the holder 12 defines a second diameter, with the second diameter being less than the first diameter. Further, in the first position, the holder 12 defines a first elliptical shape. In the second position, the holder 12 defines a second elliptical shape, with the first elliptical shape being different than the second elliptical shape. In this manner, with the holder 12 in the second position with a reduced diameter, a portion of the holder 12 contacts the sample source (i.e., the finger 19) and the actuation portion 24 of the holder 12 is able to pump and/or extract blood, as described in more detail below.

In some examples, the actuation portion 24 includes a contact member 34. With the actuation portion 24 in the first position, the contact member 34 is in a disengaged position, i.e., the contact member 34 is provided in a first position with respect to the sample source, such that the contact member 34 may be in slight contact therewith. With the actuation portion 24 in the second position, the contact member 34 is in an engaged position, i.e., the contact member 34 is provided in a second position with respect to the finger 19, such that the contact member 34 is in an applied pressure contact with the finger 19, and the actuation portion 24 of the holder 12 is able to pump and/or extract blood. For example, with the contact member 34 in the engaged position, the contact member 34 exerts a pressure on the sample source.

In some examples, the actuation portion 24 includes a pumping member 36 for applying pressure to the finger 19, such as a pair of opposed tabs or wings 38. Each wing 38 can include a contact member 34. The holder 12 can also include a living hinge portion 42. The living hinge portion 42 allows the user to squeeze the wings 38 between a first position (passive state) and a second position (active state). It is believed that use of the tabs or wings 38 to draw blood out of a patient's finger 19 minimizes hemolysis while maintaining an adequate flow of blood from the patient's finger 19. A resting position and hinge of the wings 38 are designed to maintain contact and retention with the smallest patient finger that can fit into a holder 12, while flexing to accommodate the largest patient finger within a holder 12 without blood occlusion. In some examples, the wings 38 may be positioned on the finger receiving portion 20 at a position located proximal of a patient's fingernail and distal of a patient's first knuckle to avoid hard tissues on the patient's finger 19.

The holder 12 can be configured to allow a user to repeatedly squeeze and release the wings 38 to pump and/or extract blood from a finger 19 until a desired amount of blood is filled in the collection container 16. The wings 38 are configured to flex to maintain gentle contact with a range of patient finger sizes that may be used with the holder 12 and to retain the holder 12 on the patient's finger 19. The wings 38 may also provide active pressure features for the holder 12.

In some examples, the holder 12 can include a stability extension portion 40. The stability extension portion 40 provides additional support for the holder 12 to be securely placed onto the finger 19. In one example, the finger receiving portion 20 forms a generally C-shaped member and includes a plurality of inner gripping members for providing additional grip and support for the holder 12 to be securely placed onto a patient's finger 19. The stability extension portion 40 assists in maintaining contact with the patient's finger 19 during use of the holder 12 while avoiding the blood supply and knuckles of the patient's finger 19.

The blood collection device 10 for obtaining the blood sample also includes the lancet housing or lancet 14 (shown in FIG. 1B) that is removably connectable to the port 26 of the holder 12. Referring to FIG. 1B, the lancet housing or lancet 14 can include an inlet or opening 50, an interior 52, a puncturing element 54, an engagement portion 56, a retractable mechanism 58, and a drive spring 60. The puncturing element 54 can be moveable between a pre-actuated position, wherein the puncturing element 54 is retained within the interior 52 of the lancet housing 14, and a puncturing position, wherein at least a portion of the puncturing element 54 extends through the inlet 50 of the lancet housing or lancet 14 to lance a portion of a finger 19. In one example, the lancet 14 of the present disclosure is a contact activated lancet and may be constructed in accordance with the features disclosed in U.S. Pat. No. 9,380,975, entitled "Contact Activated Lancet Device", which is incorporated herein by reference in its entirety.

In some examples, the holder 12 and the lancet housing or lancet 14 are separate components that can be removably connectable to the port 26 of the holder 12. In such examples, the lancet housing or lancet 14 includes the engagement portion 56. The lancet housing or lancet 14 can be pushed into the port 26 of the holder 12, such that the engagement portion 56 of the lancet housing or lancet 14 is locked within the locking portion 32 of the holder 12. In this manner, the lancet housing 14 is securely connected and locked to the holder 12, such that the puncturing element 54 of the lancet housing 14 can be activated to lance or puncture a sample source, e.g., the finger 19. In some examples, the port 26 of the holder 12 includes a plurality of ribs for securing and locking the lancet 14 or the collection container 16 in the port 26.

To activate the lancet 14, the lancet 14 is pushed against the finger 19 to activate the retractable mechanism 58 and drive spring 60 of the lancet 14 to lance the finger 19. After puncturing, the puncturing element 54 is immediately retracted and safely secured within the interior 52 of the lancet housing 14. Once the finger 19 is punctured, the blood sample is squeezed from the finger 19 and, as described in further detail herein, flows along a flow path into the collection container 16. Examples of structures for directing a flow of blood from a surface of the finger 19 to the sample collection container 16 are described in U.S. Patent Appl. Pub. No. 2019/0223772, entitled "Device for the Attached Flow of Blood," which is incorporated herein by reference in its entirety.

As previously described, the collection container 16 may contain the additive composition, such as a sample stabilizer or anticoagulant. As described in detail herein, the blood sample enters the sample collection container 16 and can mix with the additive composition, thereby producing a stable blood sample that can be used for various blood and analyte tests. In some examples, the collection container 16 can also include fill line(s) corresponding to a predetermined volume of sample to show the user when a sufficient volume of blood has been collected. In some examples, the sample collection container 16 can alternatively or additionally include an indicator or meter providing information about a collected volume of blood.

In order to use the capillary blood collection device 10 shown in FIGS. 1A-1E, a desired finger 19 is first cleaned and a holder 12 having an appropriate size for the desired finger 19 is selected and placed onto the finger 19 securely. Next, the lancet housing or lancet 14 is connected to the port 26 of the holder 12. As discussed previously, the lancet housing or lancet 14 is pushed into the port 26 of the holder 12, such that the engagement portion 56 of the lancet housing or lancet 14 is locked within the locking portion 32 of the holder 12. In this manner, the lancet housing or lancet 14 is securely connected and locked to the holder 12, such that the puncturing element 54 of the lancet housing 14 can be activated to lance or puncture the finger 19. With the lancet 14 connected to the port 26 of the holder 12, the lancet 14 is in communication with the finger 19.

When it is desired to activate the lancet 14 to lance the skin of the finger 19, the lancet 14 is pushed against a finger 19 to activate a retractable mechanism 58 of the lancet 14 to lance the finger 19. After the finger 19 is lanced to create blood flow from the finger 19, the lancet 14 is removed from the holder 12 and the sample collection container 16 is pushed into the port 26 of the holder 12. With the container 16 properly secured to the holder 12 for collection of a blood sample, the user repeatedly squeezes and releases the wings 38 of the holder 12 to pump and/or extract blood from the finger 19 until a desired amount of blood flows along a flow path into the collection container 16. Advantageously, with the holder 12 placed onto a finger 19, the holder 12 does not constrict the blood flow and defines lancing and finger squeezing locations. The squeezing tabs or wings 38 provide a pre-defined range of squeezing pressure that is consistently applied throughout a finger 19. By doing so, the holder 12 provides a gentle controlled finger 19 massage that stimulates blood extraction and minimizes any potential hemolysis (i.e., rupture or destruction of blood cells).

Once a desired amount of blood is collected within the sample collection container 16, a blood collector portion including the collection container 16 can be detached from the collection device 10 in order to send a collected sample to a diagnostic instrument and/or testing device. The blood collector portion can be sealed via a cap, septum, and/or lid once removed from the collection device 10 to protectively seal the blood sample within the collection container 16.

Sample Collection Container and Additive Composition

Examples of sample collection containers 16 including features for passive and/or active mixing of an additive composition with a blood sample are shown in FIGS. 2A-10B. More specifically, as previously described, the sample collection container 16 can be configured for one or more of: passive/auto mixing of the blood sample as the sample is being introduced into the container 16, active mixing achieved by creating a turbulent flow in the container 16, and/or active mixing by external manipulation of the container 16 (e.g., by a centrifuge or vortex machine). Passive/auto mixing can occur when the blood sample contacts objects or surfaces coated by and/or containing the additive composition, thereby allowing the additive composition to be released from the surface and dispersed through the blood sample. In some examples, the object or surface coated by the additive composition can be placed in a flow path between the finger 19 and an interior of the collection container 16. Accordingly, the additive composition can be dispersed into the blood flowing through the flow path and can collect in the interior of the container 16. In other examples, the additive composition can be applied to an inner surface of the container 16 and/or to a surface of an object contained within the interior of the container 16.

In some examples, the present inventors have determined that dispersion of the additive composition through the blood sample can be improved by positioning the additive composition at locations within the container 16 that reduce a distance that the blood travels before contacting the additive composition. For example, an object containing the additive composition may be adhered to an inner surface of the sidewall of the container 16 at a middle point about half way between a top and a bottom of the container. In other examples, the additive composition can be positioned proximate to a bottom of the sample collection container 16. In such cases, different agitating members, such as a rising or sinking ball, can be placed in the container 16 to help distribute the additive composition from the bottom of the container 16 throughout the blood sample.

Figure 2A:
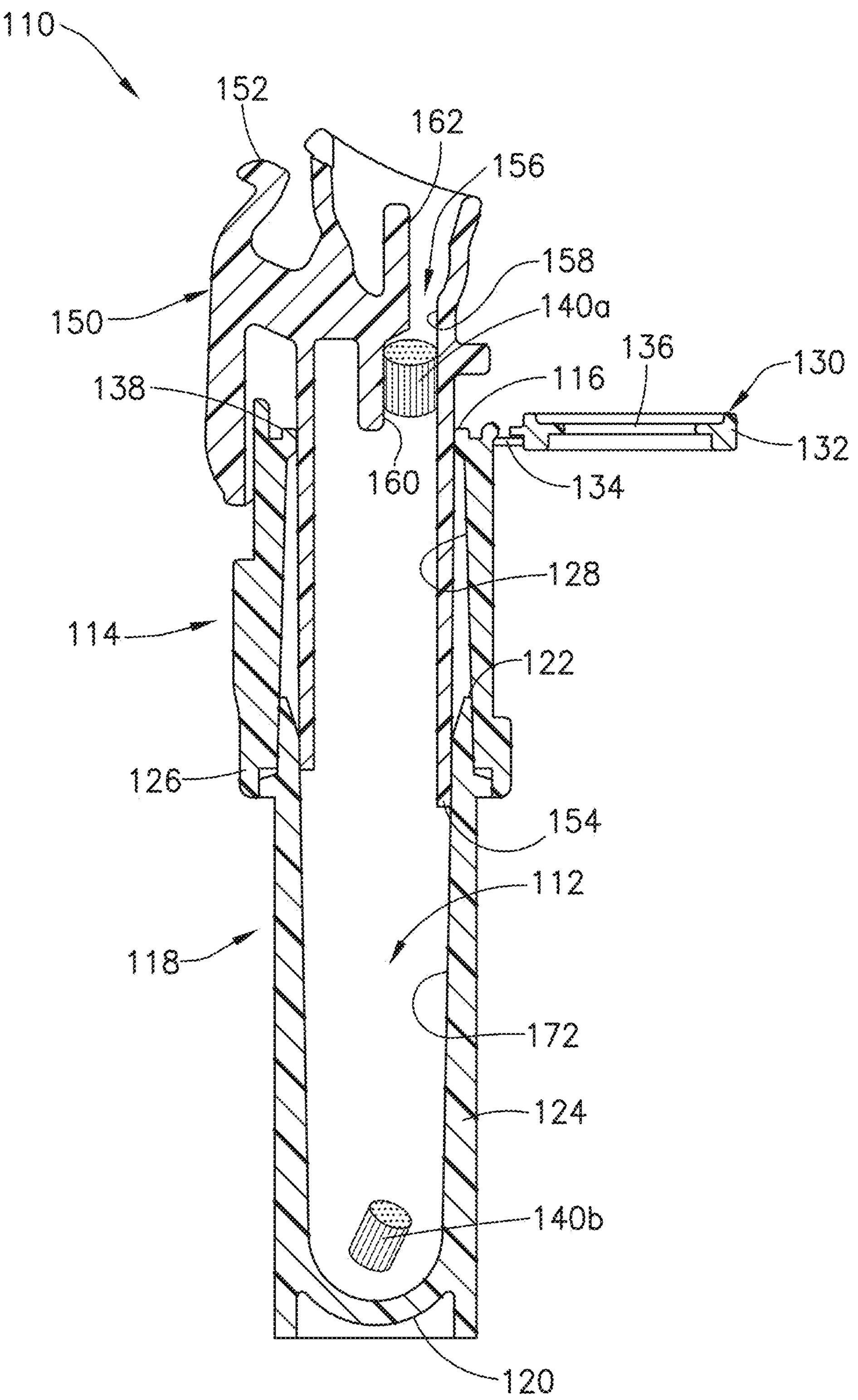
FIG. 2A is a cross-sectional view of a sample collection container including additive dispensing objects, according to an aspect of the present disclosure.
Figure 2B:
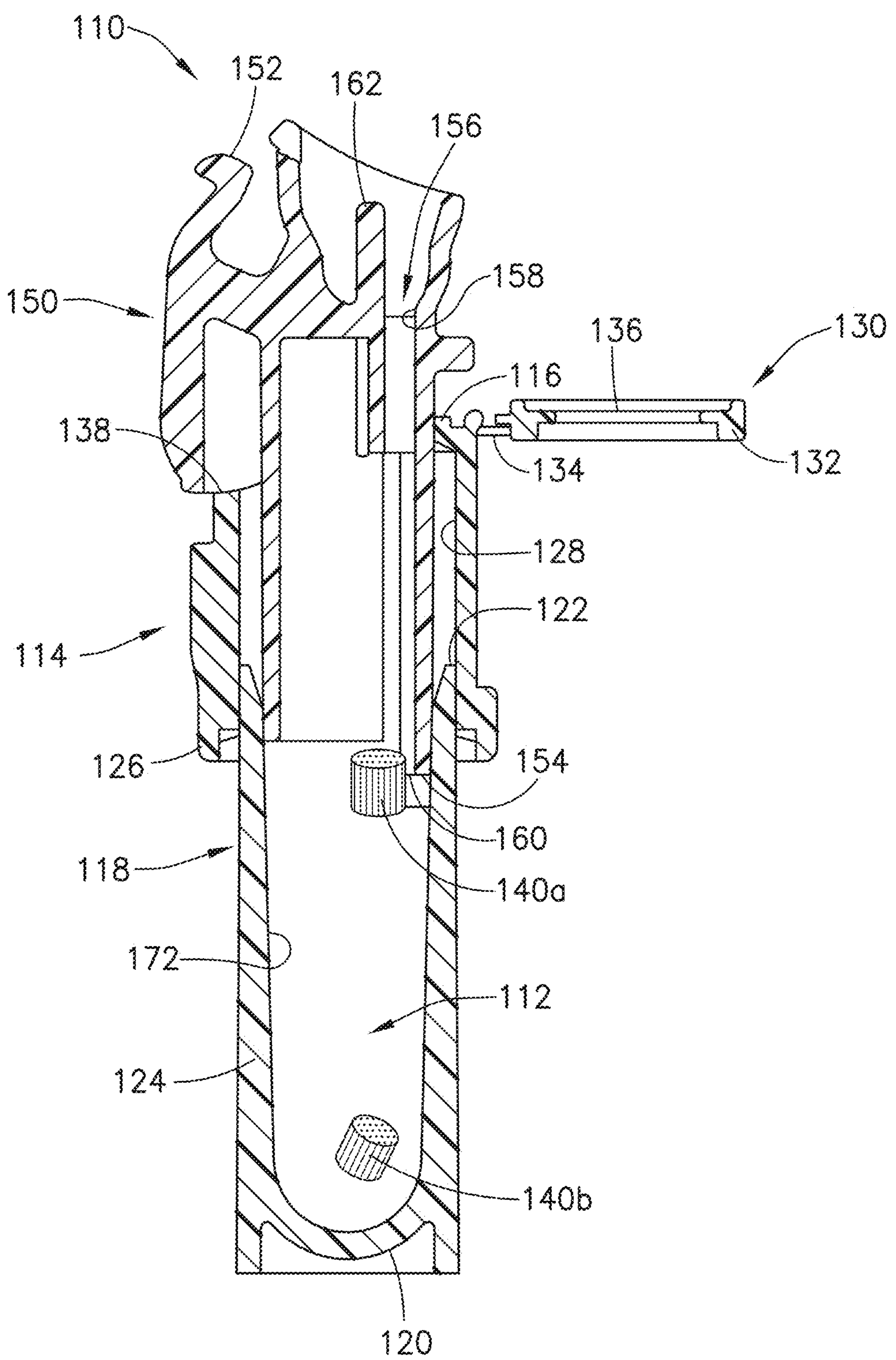
FIG. 2B is a cross-sectional view of another example of a sample collection container including additive dispensing objects, according to an aspect of the present disclosure.

With specific reference to FIGS. 2A and 2B, in some examples, the sample collection container 16 of the present disclosure includes a housing 150 comprising a first end 152, a second end 154, a flow channel 156 having an inlet 158 and an outlet 160 extending at least partially between the first end 152 and the second end 154 of the housing 150. The housing 150 can also include one or more flow directing protrusions 162, such as a pillar, post, fin, blade, or another elongated member, adjacent to the inlet 158 for directing blood from the port 26 of the blood collection device 10 into the flow channel 156. In particular, the flow directing protrusion 162 provides a fluid attachment point or surface. Blood from the patient's finger 19 is drawn towards the surface by adhesion forces. The blood then moves along the surface of the protrusion 162 towards the flow channel 156 by gravity. The blood flows through the channel 156 into an interior or cavity 112 of the container 110. The blood can be drawn through the flow channel 156 by forces including gravity, a negative pressure or vacuum force, and/or capillary action. The housing 150 can also include flow directing or fluid attachment structures (not shown) near the outlet 160 of the flow channel 156, which assist in drawing blood from the flow channel 156 into an interior 112 of the container 16.

The container 16 also includes a container body 110 removably connected to the housing 150. For example, the second end 154 of the housing 150 can be inserted into or over the container body 110. The container body 110 defines the interior or cavity 112 configured to receive the blood sample from the port 26 of the holder 12. The container cavity 112 can have a volume of, for example, about 50 μL to about 500 μL. The container body 110 can be a two-piece enclosure including an upper portion 114 or cap having an open or partially open top 116 and a lower portion 118 (also referred to herein as a base or body) having a closed bottom 120. The upper portion 114 and the lower portion 118 can include annular or interior walls 124, 128 extending between the open top 116 and the closed bottom 120 of the container body 110.

The upper portion 114 or cap and the lower portion 118 can be separate components that can be removably connected together and can be disassembled by, for example, twisting the upper portion 114 or cap relative to the lower portion 118 and/or by pulling the upper portion 114 or cap axially away from the lower portion 118. In some examples, the lower portion 118 of the container body 110 can include the closed bottom 120, a lower portion open top 122, and a lower portion annular sidewall 124 extending therebetween. Similarly, the upper portion 114 or cap can include an open bottom 126 inserted over the open top 122 of the lower portion 118, the upper portion open top 116, and an upper portion annular sidewall 128 extending therebetween.

Desirably, the upper portion 114 or cap and the lower portion 118 of the container body 110 should be securely connected together to protect the blood sample in the interior or cavity 112 of the container body 110. In particular, the connection or interface between the portions 114, 118 may need to be sufficiently secure and robust enough to withstand foreseeable misuse without allowing leakage or separation of the upper portion 114 or cap from the lower portion 118 at inappropriate or unexpected times. At appropriate times, the connection or interface between the upper portion 114 or cap and the lower portion 118 should be easy to overcome in a controlled manner, thereby allowing users to easily access the blood sample contained in the interior 112 of the container body 110.

In other examples, the upper portion 114 and the lower portion 118 can be integrally formed and/or non-removably attached together by, for example, an adhesive or ultrasonic welding. In some examples, the container body 110 can be a single-piece or integral structure including the open top 116, closed bottom 120, and an integral or monolithic interior wall 124 extending between the top 116 and the bottom 120.

The sample collection container 16 further includes a lid 130 including a lid body 132, a flexible connection, such as a hinge 134 or living hinge, a pierceable septum 136, and a latch 138. The flexible connection or hinge 134 is connected between the lid body 132 and the upper portion 114 or cap of the container body 110. The hinge 134 is a flexible member that is configured to open and close, thereby moving the lid 130 between a closed position, in which the lid 130 covers the open top 116 of the upper portion 114 or cap and an open position (shown in FIGS. 2A and 2B), where the open top 116 of the upper portion 114 or cap is uncovered. Various structures of flexible connections or hinges 134 that can be formed from rigid or semi-rigid materials will be known to those skilled in the art, which can be adapted for use with the collection container 16 of the present disclosure. For example, the hinge 134 can be an elongate member including one or more notches or scored lines that provide a bend point for the hinge 134. The hinge 134 is configured to pivot or unfold about the bend point, thereby allowing the lid 130 to transition between the closed position and the open position.

In some examples, the pierceable septum 136 is mounted to the lid body 132 and seals the open top 116 of the upper portion 114 when the lid 130 is in the closed position. A latch can extend from the lid body 132 and, when the lid 130 is in the closed position, engages a protrusion or catch 138 on the upper portion 114 or cap of the container body 110 to secure the lid 130 remains in the closed position.

In some examples, the sample collection container 16 further includes the additive dispersing object 140 positioned to be contacted by blood flowing from the port 26 of the blood collection device 10, through the flow channel 156, and/or into the collection cavity 112. As previously described, the additive dispersing object 140 includes (e.g., is coated by and/or impregnated with) the additive composition to be mixed with the blood sample. As previously described, the additive composition can include the anticoagulant, such as EDTA or Heparin, as well as other sample stabilizing compositions.

In some examples, the additive dispersing object 140 is a cylindrical structure, such as a cylindrical structure having a height of about 2 mm to about 8 mm and a diameter of about 3 mm to about 6 mm. The dispersing object 140 can be formed from an open cell foam or a closed cell foam that is impregnated with the additive composition. The porosity of the foam could range from 50-80%. In some preferred examples, the additive dispersing object 140 is formed from an open cell foam comprising at least one of melamine or formaldehyde-melamine-sodium bisulfite copolymer. The open cell foam can also be a hydrophilic open cell foam, configured to absorb blood, thereby bringing the blood sample into contact with the additive composition coated on or impregnated in the foam structure. In some examples, the foam object can be formed from multiple foam strands or cylindrical members compressed together to form a substantially cylindrical member. In some examples, the dispersing object 140 comprises a hollow tubular structure. For example, the dispersing object 140 can comprise a hollow tubular structure, such as a hollow cylindrical tube, of foam formed by an extrusion process.

As previously described, the additive dispersing objects can be positioned at a variety of locations within or proximate to the flow channel 156 and/or the container cavity 112. For example, as shown in FIG. 2A, the sample collection container 16 includes a first additive dispersing object 140*a* positioned in the flow channel 156 proximate to the inlet 158 of the flow channel 156. The container 16 also includes a second additive dispersing object 140*b* positioned proximate to the bottom 120 of the lower portion 118 of the container body 110. In use, the blood sample enters the flow channel 156, passes around or through the first additive dispersing object 140*a*, which can be formed from a porous and permeable material, such as open cell foam, and then enters the cavity 112 of the container body 110 through the outlet 160 of the flow channel 156. The blood sample then falls through the container cavity 112 by gravity, collecting in the bottom 120 of the lower portion 118. Once in the bottom 120 of the container body 110, the blood sample contacts the second additive dispersing object 140*b*. When the collected blood sample is agitated, the additive composition of the second additive dispersing object 140*b* can be dispersed through the blood sample, thereby providing a mixed sample including a higher concentration of the additive composition than if only one additive dispersing object 140*a* were present.

FIG. 2B shows another exemplary container 16 including the housing 150 inserted into the container body 110. As in previous examples, the container 16 of FIG. 2B also includes the first additive dispersing object 140*a*. However, unlike in the previous example, the additive dispersing object 140*a* in FIG. 2B is positioned proximate to the outlet 160 of the flow channel 156. Similar to FIG. 2A, the sample collection container 16 also includes the second additive dispersing object 140*b* positioned proximate to the bottom 120 of the lower portion 118 of the container body 110. As in the previous examples, the blood sample flows through the flow channel 156, passing through the outlet 158, and through or about the first additive dispersing object 140*a*. The blood sample then collects in the bottom 120 of the lower portion 118 of the container body 110, where it contacts and mixes with the additive composition of the second additive dispersing member 140*b*.

Figures 2C, 2D:
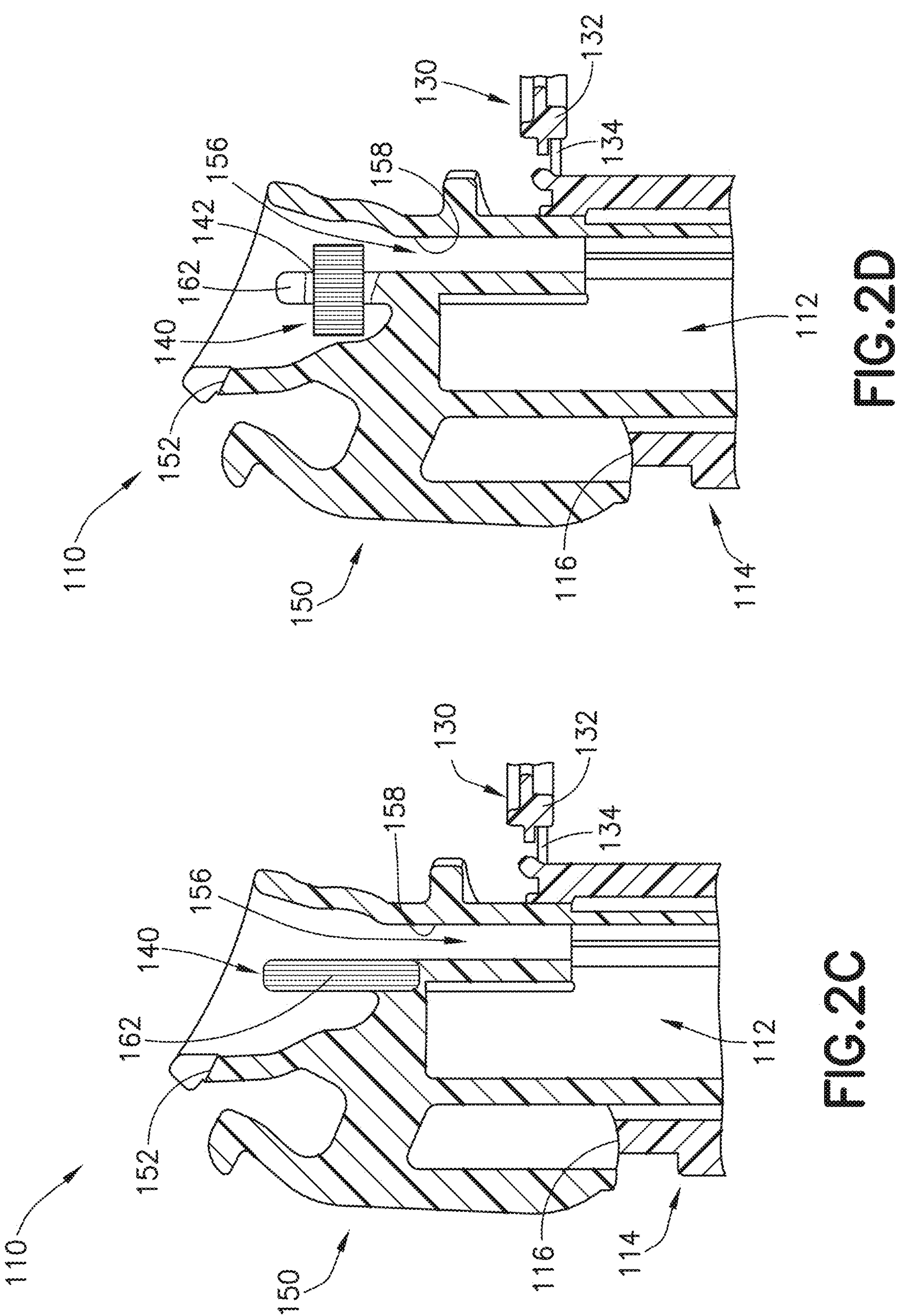
FIG. 2C is a cross-sectional view of a housing of another example of a sample collection container, according to an aspect of the present disclosure.
FIG. 2D is a cross-sectional view of a housing of another example of a sample collection container, according to an aspect of the present disclosure.

FIG. 2C shows another example of the container housing 150. In FIG. 2C, an additive dispersing member 140 is an elongated cylindrical member that forms a portion of and/or covers the fluid directing protrusion 162 of the housing 150. As previously described, the fluid directing protrusion 162 is positioned such that blood from the patient's skin is drawn against the fluid directing protrusion 162. The blood slides along the protrusion 162 coming into contact with the additive composition of the additive dispersing object 140. Due to the contact with the blood, the additive composition releases from the protrusion 162 and mixes with the blood forming a mixed sample. The mixed sample of the blood and additive composition is then drawn into the flow channel 156. The mixed blood sample progresses through the flow channel 156 by gravity and/or by capillary action forces and is then expelled from the outlet 160 of the flow channel 156 into the container cavity 112.

Figure 2E:
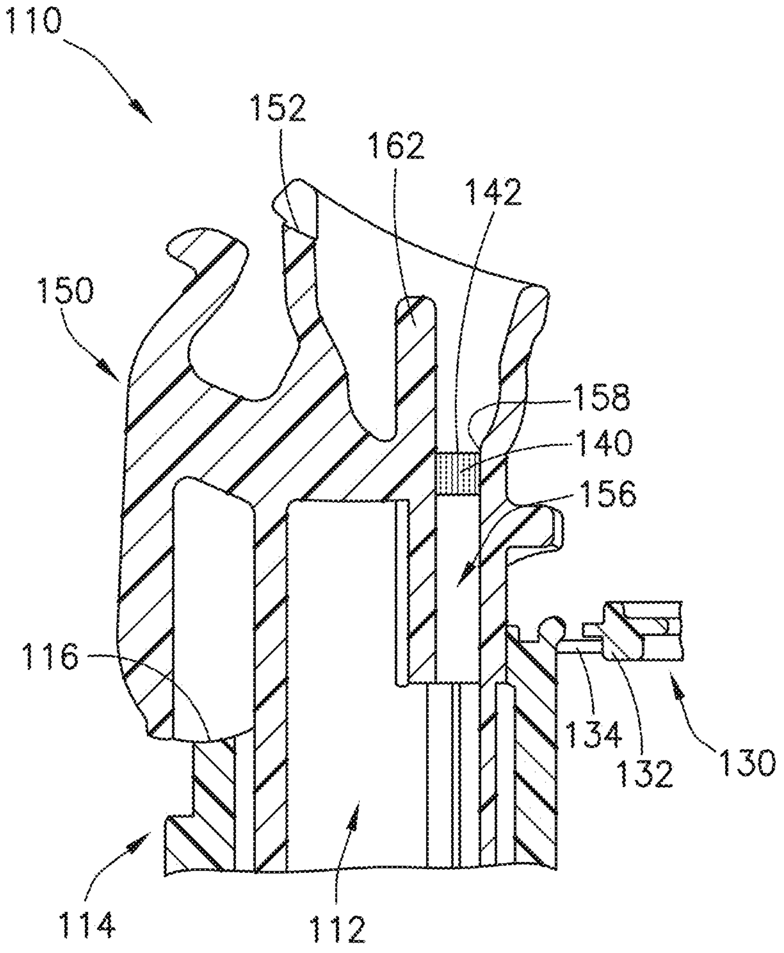
FIG. 2E is a cross-sectional view of a housing of another example of a sample collection container, according to an aspect of the present disclosure.

In some examples, as shown in FIG. 2D, the additive dispersing object 140 can be a donut shaped, annular, or partially annular member including a central opening 142. The central opening 142 can be sized to correspond to an outer diameter of the fluid directing protrusion 162, such that the additive dispersing object 140 can be inserted over and remain in place relative to the fluid directing protrusion 162. In other examples, as shown in FIG. 2E, the annular or partially annular dispersing object 140 can be positioned at the inlet 158 to the flow path 156, such that blood passes through the central opening 142 of the annular additive dispersing object 162 and into the flow path 156.

In some examples, instead of being positioned in or proximate to the flow channel 156, the additive dispersing object 140 can be positioned in the container cavity 112 of the container body 110, such as adjacent to the inner wall 124 of the lower portion 118 or near the closed bottom 120 of the lower portion 118 of the container body 110. In order to properly disperse or mix blood and the additive composition, the sample collection container 16 may include various mechanical or external agitation mechanisms for ensuring that blood flows past or through the additive dispersing object 140 and that the additive composition is dispersed throughout the blood sample.

Figure 3:
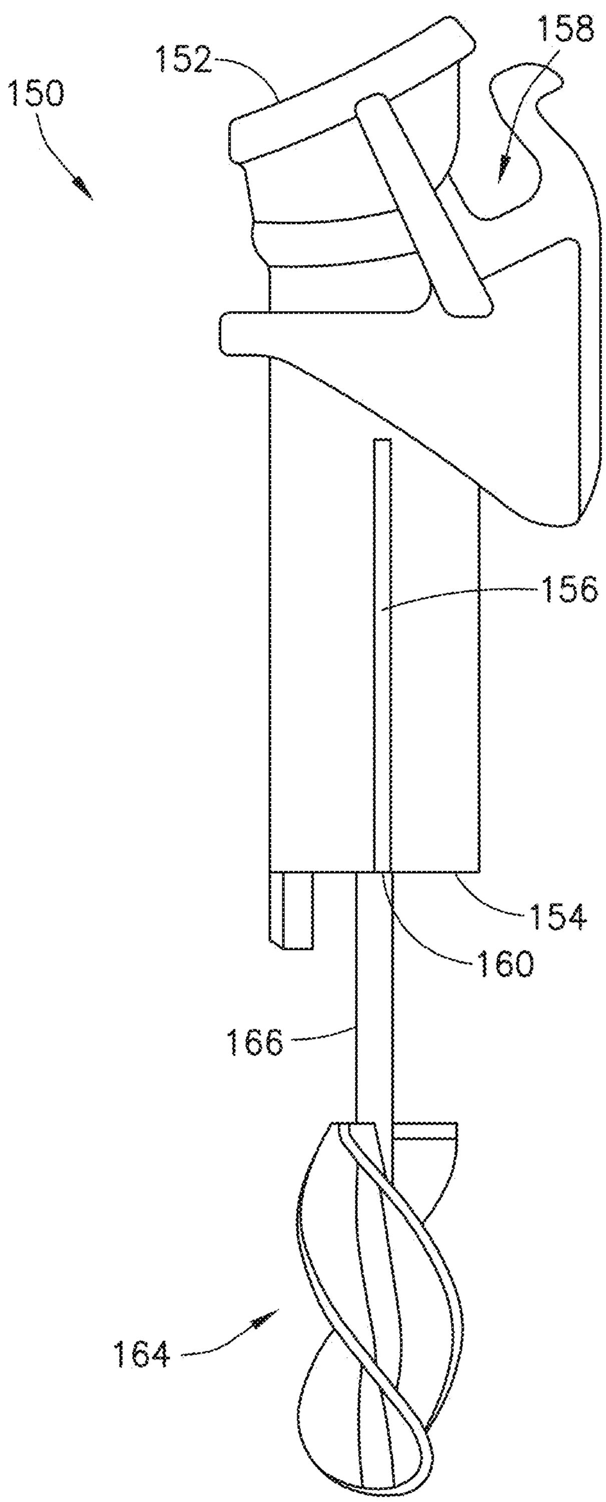
FIG. 3 is a side view of another example of a sample collection container, according to an aspect of the present disclosure.

For example, as shown in FIG. 3, the sample collection container 16 can include an agitation tool 164 for agitating blood as it is expelled from the flow channel 156 and into the container cavity 112. As shown in FIG. 3, the agitation tool 164 can be a fin or blade, such as a helical fin or blade extending about an elongated member or post 166. In use, blood expelled through the outlet 160 of the flow channel 156 contacts the fin or blade causing the fin or blade to rotate about the post 166. The rotation of the fin or blade agitates and mixes the blood and additive composition, thereby providing a well-mixed sample.

Figures 4A, 4B, 4C:
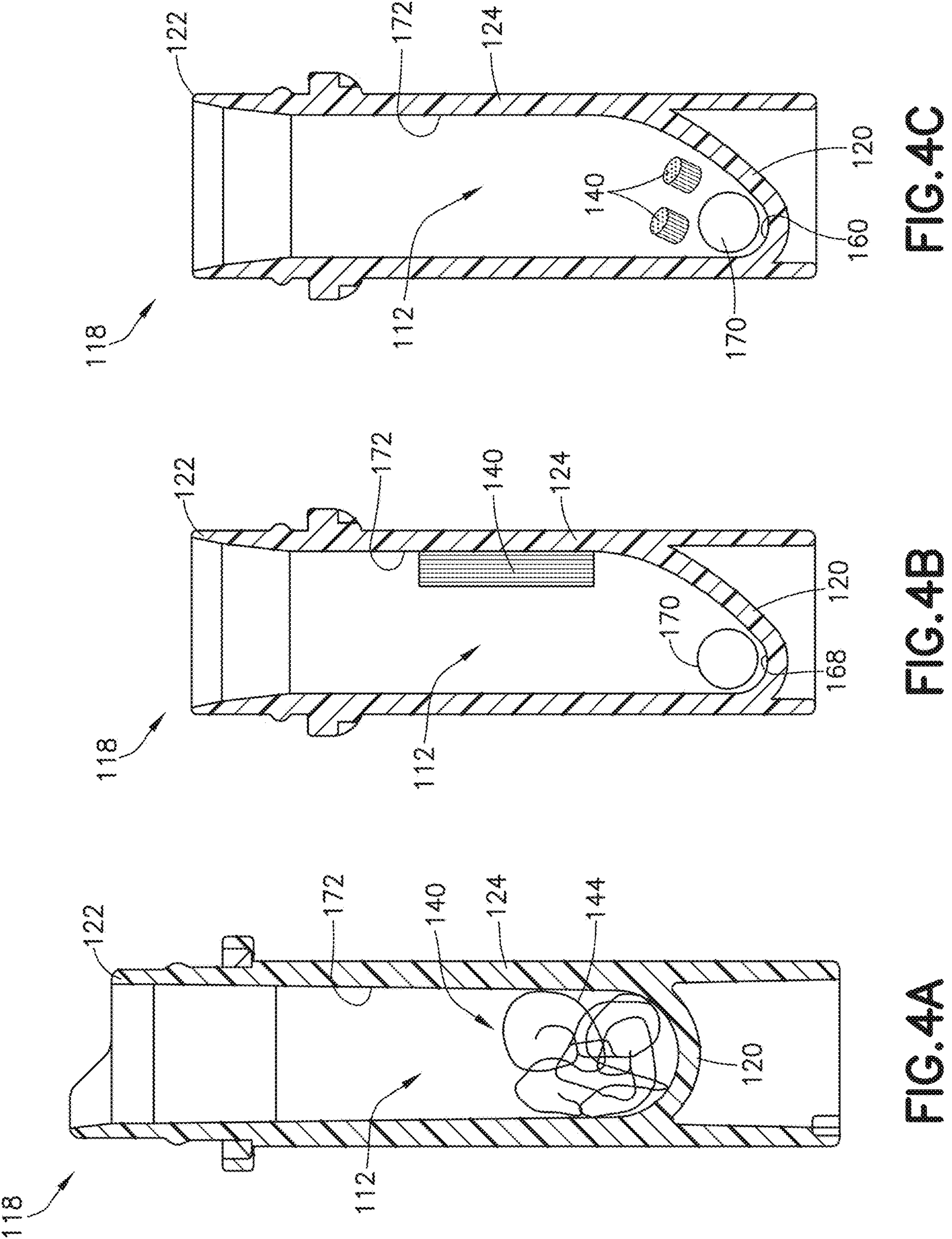
FIG. 4A is a cross-sectional view of another example of a sample collection container, according to an aspect of the present disclosure.
FIG. 4B is a cross-sectional view of another example of a sample collection container, according to an aspect of the present disclosure.
FIG. 4C is a cross-sectional view of another example of a sample collection container, according to an aspect of the present disclosure.

With reference to FIG. 4A, in some examples, the additive dispersing object 140 disposed near the bottom 120 of the container body 110 can be a flexible and/or bendable elongated member 144, such as a length of string, thread, ribbon, or wire. The flexible elongated member 144 can be coated and/or impregnated with the additive composition. As shown in FIG. 4A, the elongated member 144 is positioned in the container cavity 112 in a disordered or unwound arrangement in which the elongated member 144 bends or coils in many directions. The disordered arrangement creates many spaces, cavities, and crevasse around the elongated member 144, meaning that blood can easily pass through portions of the elongated member 144 contacting and mixing with the additive composition coated on the elongated member 144.

FIGS. 4B and 4C show additional arrangements of cylindrical additive dispersing objects 140 positioned in the lower portion 118 of the container body 110. As in previous examples, the additive dispersing objects 140 of FIGS. 4B and 4C can be formed from a porous foam material, such as melamine open cell foam. The container body 110 of FIGS. 4B and 4C differ from previous examples in that the bottom 120 of the lower portion 118 of the container body 110 slopes towards the interior wall 124 of the lower portion 118 of the container body 110 forming a depression 168 that can be sized to receive the additive dispersing object 140. The sloped bottom 120 of the container body 110 can be configured such that, when the additive dispersing object 140 is positioned in the depression 168, an elongated sensor, probe, tool, or similar sensor device can be inserted into the container cavity 112 to analyze the blood sample without contacting the additive dispersing object 140. The containers 16 of FIGS. 4B and 4C also include an agitation member 170, such as a buoyant or heavy object, configured to float or sink through the blood sample to agitate and/or assist in dispersing the additive composition through the blood sample. The agitation member 170 can be any shape and size that fits in the container cavity 112 and can move through the container cavity 112 without restriction. For example, the agitation member 170 can be a ball, sphere, cube, ellipsoid, cylinder, or any other convenient shape. The agitation member 170 can be formed from any suitable buoyant material that floats in blood, such that the agitation member moves through the container in an upward direction as the blood sample is expelled from the outlet 160 and into the container cavity 112. The agitation member 170 can also be formed from a heavy material (i.e., a material that is denser than blood), such that the heavy agitation member 170 moves through the container cavity 112 in a downward direction as the blood sample is introduced into the container cavity 112.

In other examples, as shown in FIG. 4B, the additive dispersing object 140 can be an elongated cylinder that is adhered to an inner surface 172 of the interior wall 124 of the container body 110. For example, the additive dispersing object 140 can be adhered to the sidewall 124 near the middle of the lower portion 118 of the container body 110, approximately half way between the open top 122 and the bottom 120 of the lower portion 118 of the container body 110, or at any other convenient location on the interior walls 124, 128 of the upper or lower portions 114, 118 of the container body 110. The additive dispersing member 140 can be adhered to the interior wall 124 using any biocompatible adhesive, as known in the art, which does not interact with or degrade the blood sample contained in the container cavity 112. As shown in FIG. 4B, the agitation member 170, such as the floating or sinking ball, rests in the depression 168 formed by the sloped bottom 120 of the container body 110. In use, the blood passes through the outlet 160 of the flow channel 156, along the inner surface 172 of the interior wall 124 of the lower portion 118 of the container body 110, around or through the additive dispersing member 140, and collects in the bottom 120 of the container body 110. As the blood collects, the agitation member 170 moves around the container body 110 thereby enhancing agitation of the blood sample and, in particular, causing the additive composition to release from the additive dispersing object 140 and to disperse through the collected blood sample.

In FIG. 4C, the container 16 includes two additive dispersing objects 140, specifically two small cylinders positioned proximate to the bottom 120 of the container body 110. The agitation member 170, such as the sinking or floating ball, is also positioned in the depression 168 formed by the sloped bottom 120 of the container body 110, as in previous examples. In use, blood is expelled from the outlet 160 of the flow channel 156 into the container cavity 112. As the blood collects in the container cavity 112, the additive dispersing objects 140 and the agitation member 170 move through the container cavity 112 causing the additive composition to release from and disperse through the collected blood sample. In particular, the agitation member 170 can move through the blood sample in either an upward direction (when the agitation member 170 is formed from a material that is less dense than blood) or in a downward direction (when the agitation member 170 is formed from a material that is heavier than blood), which causes the additive composition to disperse through the blood sample.

Figure 5A:
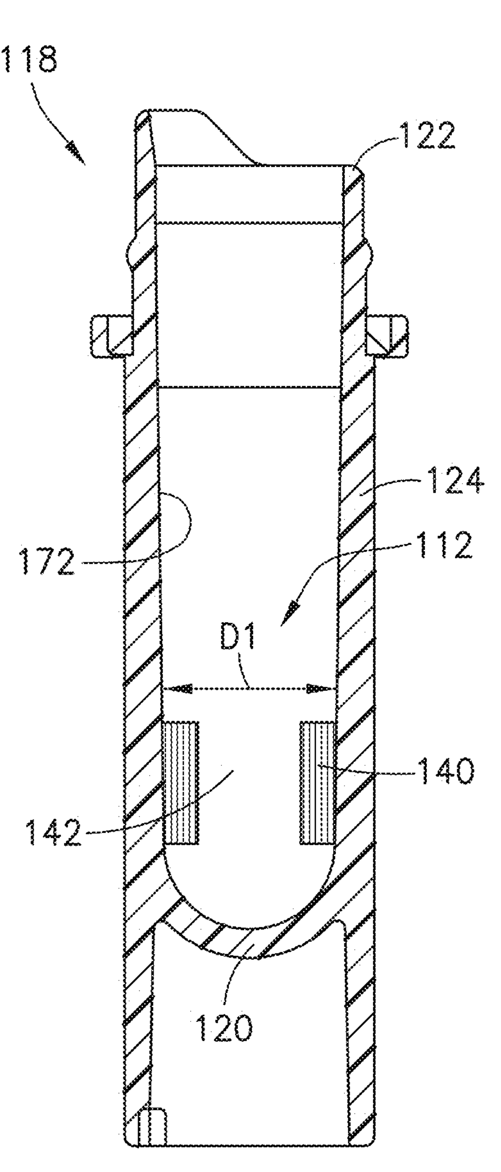
FIG. 5A is a cross-sectional view of another example of a sample collection container, according to an aspect of the present disclosure.
Figure 5B:
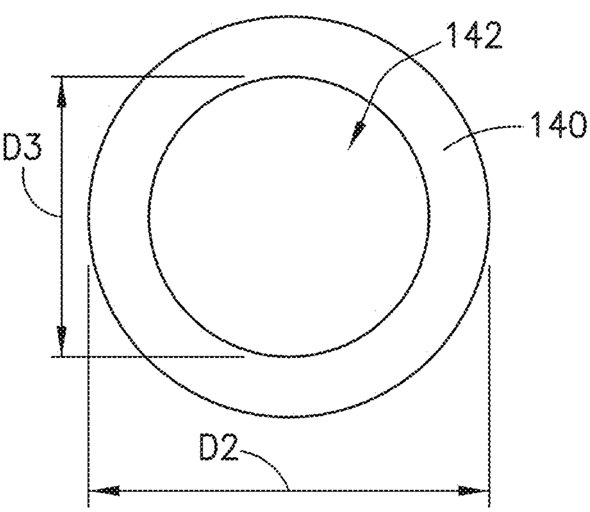
FIGS. 5B and 5C are top views of different additive dispersing objects, according to aspects of the present disclosure.
Figure 5C:
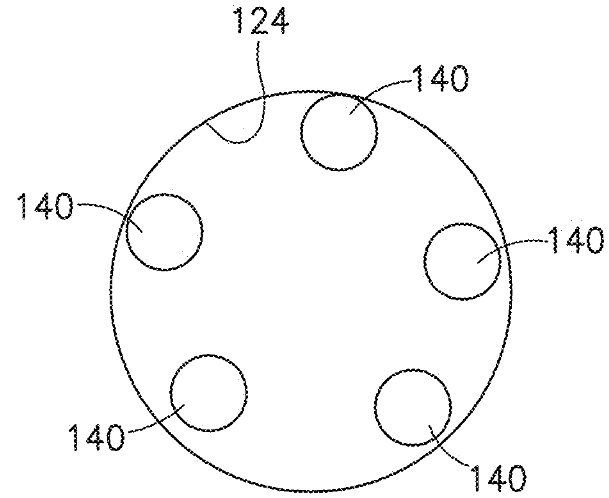

With reference to FIGS. 5A and 5B, in some examples, the additive dispersing object 140 can include a larger donut-shaped, annular, or semi-annular member. The annular member can have a peripheral edge with an outer diameter D2 that corresponds to an inner diameter D1 of the interior wall 124 of the lower portion 118 of the container body 110, and a central opening 142 with a diameter D3. Accordingly, the annular additive dispersing object 140 can be positioned against the inner surface 172 of the interior wall 124, such that blood passing along the inner surface 172 of the interior wall 124 passes through or around the additive dispersing object 140 as the blood moves in a downward direction towards the bottom 120 of the container cavity 112 by gravity. As shown in FIG. 5C, in other examples, the additive dispersing object 140 can include multiple elongated cylindrical members adhered to the inner surface 172 of the interior wall 124 arranged to form a ring. For example, as shown in FIG. 5C, there are five cylindrical members arranged to form the ring; while, in other examples, fewer or more than five cylinders can be used to form the ring. As in previous examples, the cylindrical members can be adhered to the inner surface 172 of the interior wall 124 by any convenient biocompatible adhesive, as are known in the art.

In some examples, as shown in FIGS. 6A-7C, the additive dispersing object 140 includes structures that position the additive dispersing object 140 near to a middle of the lower portion 118 of the container body 110, approximately halfway between the open top 122 and the closed bottom 120 of the lower portion 118. The additive dispersing objects 140 of FIG. 6A-7C can be formed from rigid materials, such as rigid plastic. The additive dispersing objects 140 can be formed by known manufacturing processes for plastic parts, such as by injection molding. The additive dispersing object 140 can also include open or closed cell foam portions, as in previous examples. The additive dispersing objects 140 of FIG. 6A-7C can be coated with the additive composition by, for example, spraying the additive composition on the molded part, immersing the molded part in a solution of the additive composition, or by other known methods for applying a coating to a molded part. Positioning the additive dispersing object 140 in the middle of the lower portion 118 of the container body 120 decreases the distance that the blood travels before it mixes with the additive composition. Specifically, as shown in FIG. 6A, blood expelled from the outlet 160 of the flow channel 156 contacts the additive dispersing object 140 as it moves along the inner surface 172 of the interior wall 124 of the lower portion 118. In contrast, in examples where the additive dispersing object 140 is proximate to the bottom 120 of the container body 110, blood collects at the bottom of the container body 110 meaning that once the additive dispersing object 140 is submerged or partially submerged, less blood comes into contact with the additive dispersing object 140, which reduces an amount of the additive composition dispersed through the blood sample.

As shown in FIGS. 6A and 6B, the additive dispersing object 140 can include a circular disk 174 (shown in FIGS. 6A and 6B) or a partially circular disk 174 (shown in FIG. 6C) sized to fit within the collection cavity 112 of the container body 110 to stabilize the object 140 within the container cavity 112 in an upright orientation. The disk 174 includes a peripheral edge 176 that entirely or partially matches or substantially corresponds to a curvature of the inner surface 172 of the interior wall 124 of the lower portion 118 to maintain positioning of the disk 174 within the container cavity 112. As used herein, a partially circular disk 174 (as shown in FIG. 6C) refers to a disk 174 where portions or segments of the peripheral edge 176 of the disk 174 are curved or arcuate, matching a curvature of the inner surface 172 of the interior wall 124. As shown in FIG. 6C, the disk 174 can also include cutout portions 178, where the peripheral edge 176 of the disk 174 does not match the inner surface 172 of the wall 124. In some examples, the disk 174 can also include a central opening 180, allowing the blood sample to pass through the disk 174 to improve distribution of the additive composition through the blood sample.

In some examples, the additive dispersing object 140 further includes posts 182 extending from either an upper surface 184 or a lower surface 186 of the disk 174. The posts 182 can have a cross section that is shaped like a cross or "x", which increases the surface area of the posts 182 compared to posts having a regular circular or square-shaped cross section. As shown in FIGS. 6A and 6B, the additive dispersing object 140 can include four posts 182 extending in an upward direction from the upper surface 184 of the disk 174 (referred to herein as upper posts). As shown in FIG. 6C, in other examples, the additive dispersing object 140 can include four upper posts 182 extending from the upper surface 184 of the disk 174 and four posts 182 extending from the lower surface 186 of the disk 174 in a downward direction (referred to as lower posts).

Figures 7A, 7B, 7C:
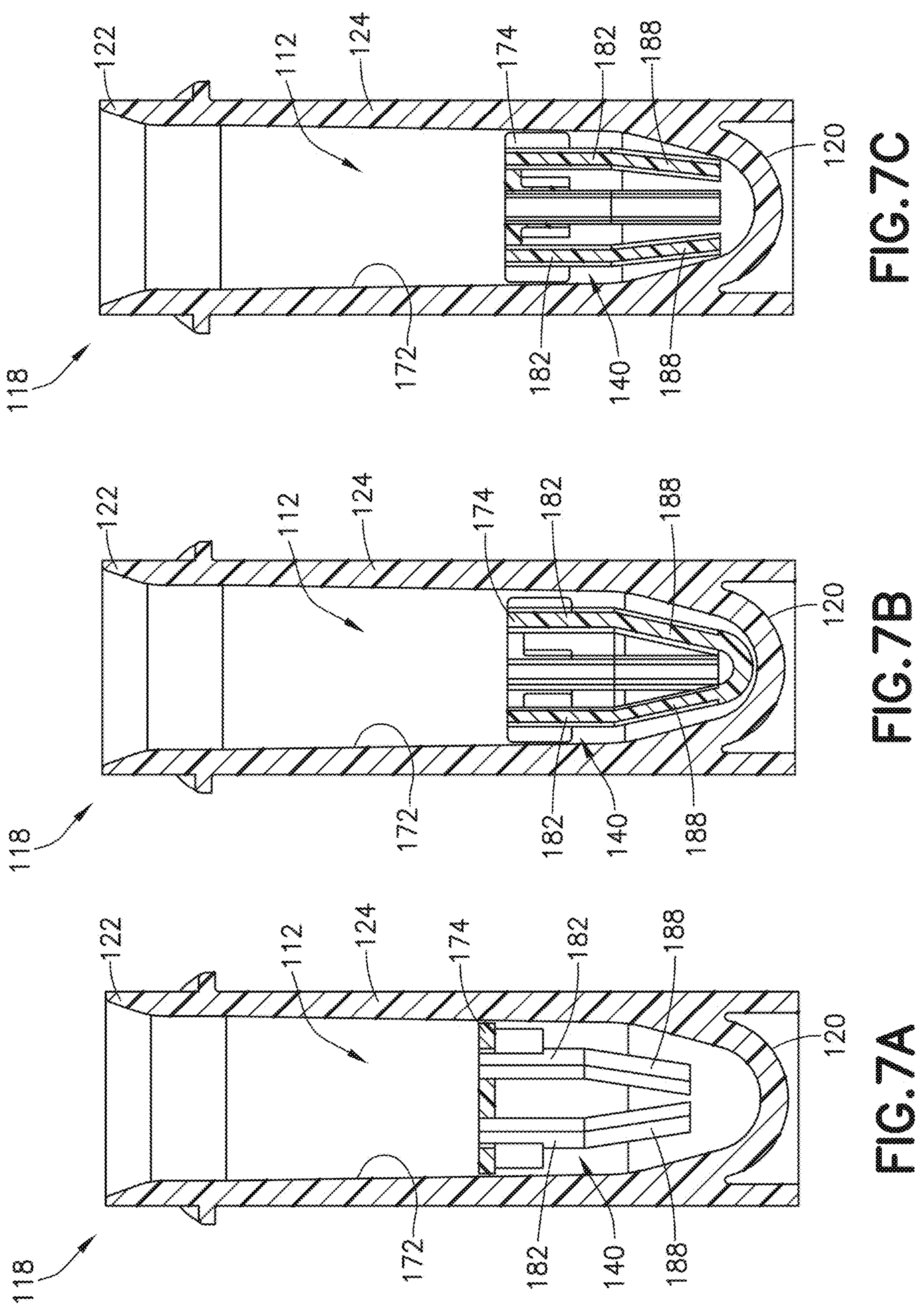
FIGS. 7A-7C are cross-sectional views of additional examples of sample collection containers, according to aspects of the present disclosure.

FIGS. 7A-7C show additional examples of the additive dispersing objects 140 that include the disks 174 and posts 182 disposed in the container body 112. As shown in FIGS. 7A-7C, in some examples, the lower posts 182 extending from a lower surface 186 of the disk 174 can include radially inwardly angled free or distal ends 188. The distal ends 188 of the different posts 182 can contact or nearly contact each other forming, in effect, a retention area or basket. The container 16 can also include an agitation member 170 (shown in FIGS. 4A-4C), such as one of the previously described floating or sinking balls, formed from material that float or sink in blood. In some examples, the agitation member 170 can be retained by the inwardly directed distal ends 188 of the posts 182 and/or retained within the basket or retention area created by the distal ends 188 of the posts 182. The agitation member 170 can be configured to move through the container cavity 112 to agitate the blood sample and to increase distribution of the additive composition through the blood sample.

Active Mixing of Sample Collection Containers

In some examples, mixing is achieved by creating turbulent flow in the sample collection container 16 to uniformly distribute the additive composition throughout the blood sample and to stabilize the blood sample. Any of the previously described sample collection containers 16 including the additive dispersing objects 140 can be used with mixing machines 210*a*, 210*b* (shown in FIGS. 8A-10B), such as a centrifuge, vortex machine or magnetic stirrer machine, as are known in the art, to create turbulent flow for a collected blood sample. In other examples, the additive composition can be sprayed on the inner surface 172 of the interior walls 124, 128 of the sample collection container 16. In either case, the turbulent flow created by the mixing machine causes the additive composition to release from the surface of the additive dispersing object 140 and/or wall 124, 128 and to distribute through the blood sample, thereby improving stability of the blood sample.

In use, a blood sample is introduced into the interior or container cavity 112 of the container body 110 through the flow channel 156 of the housing 150, as previously described. The additive composition from the inner surface 172 of the container body 112 or from the additive dispersing object 140 is dissolved into the blood sample as the blood contacts the additive composition. Once the blood collection is completed and an appropriate volume of the blood sample has been obtained, the sample collection container 16 can be removed from the port 26 (shown in FIGS. 1A-1E) of the blood collection device 10 (shown in FIGS. 1A-1E). The lid 130 can then be moved to the closed position covering the open top 116 of the cap or upper portion 114 to seal the sample collection container 16. The sealed sample collection container 16 can then be attached or engaged to a mixing machine, such as by inserting the bottom 120 of the container body 112 into a port or receptacle 214 of a mixing machine (referred to as an upright orientation). In other examples, the upper portion 114 of the container 16 can be inserted into the receptacle 214 (referred to as an inverse or reversed orientation). When activated, the mixing machine mixes the collected blood sample by creating turbulent flow in the container cavity 112 either through vibration, as shown in FIGS. 8A and 8B, or with a magnetically driven stirring action, as shown in FIGS. 9A-10B.

Figure 8A:
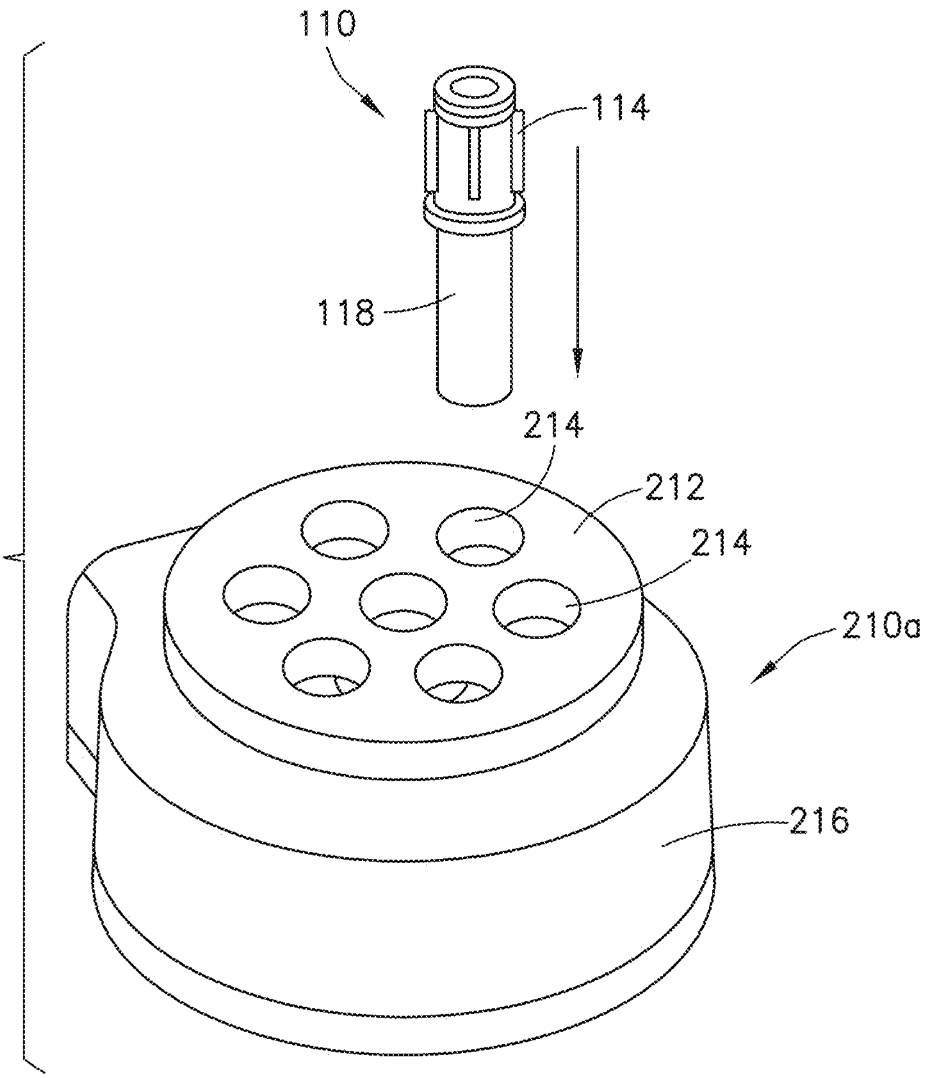
FIGS. 8A and 8B are schematic drawings showing a sample collection container being inserted into a centrifuge, according to aspects of the present disclosure.
Figure 8B:
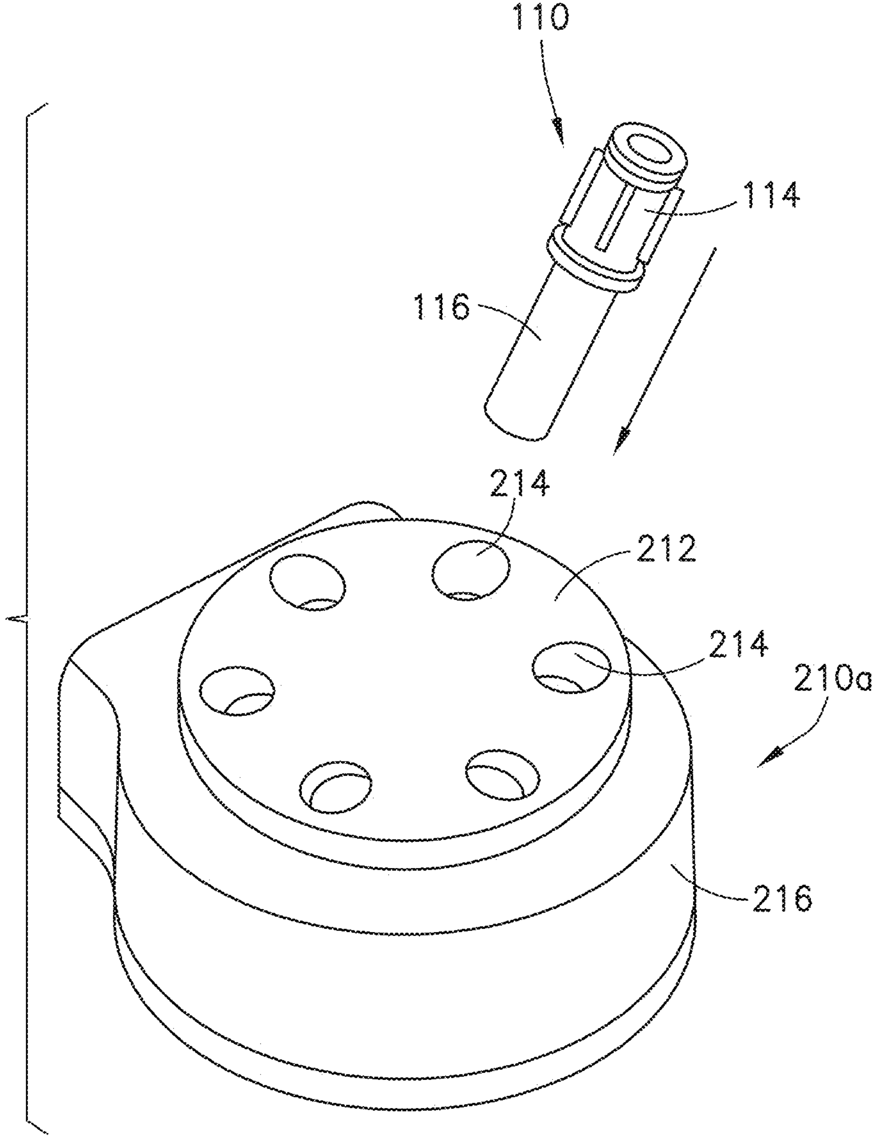

Schematic drawings of centrifuges or vibrating mixing machines 210*a* are shown in FIGS. 8A and 8B. As shown in FIGS. 8A and 8B, the vibrating mixing machine 210*a* includes a tray 212 with multiple receptacles 214 sized to receive the bottoms 120 of sample collection containers 16. The mixing machine 210*a* also includes a housing 216 or base positioned below the tray 212 sized to contain electronic components of the mixing machine 210*a*, such as a motor and associated mechanical linkages operably connecting the motor to the tray 212. When the motor is actuated, the motor causes the tray 212 to move in a forward/backward and/or side to side path to vibrate the blood sample in the container 16. As shown in FIG. 8A, the port or receptacle 214 is sized to receive the sample collection container 16 in an upright or vertical orientation. In contrast, in FIG. 8B, the ports or receptacles 214 are sized to receive the sample collection container at an angled orientation, in which the sample collection container is angled relative to the horizontal by an angle $\alpha$1. As described in further detail herein, for reverse centrifugation, the angle $\alpha$1 can be from about 65 degrees to about 85 degrees to contribute to proper mixing of the blood sample.

Figure 9B:
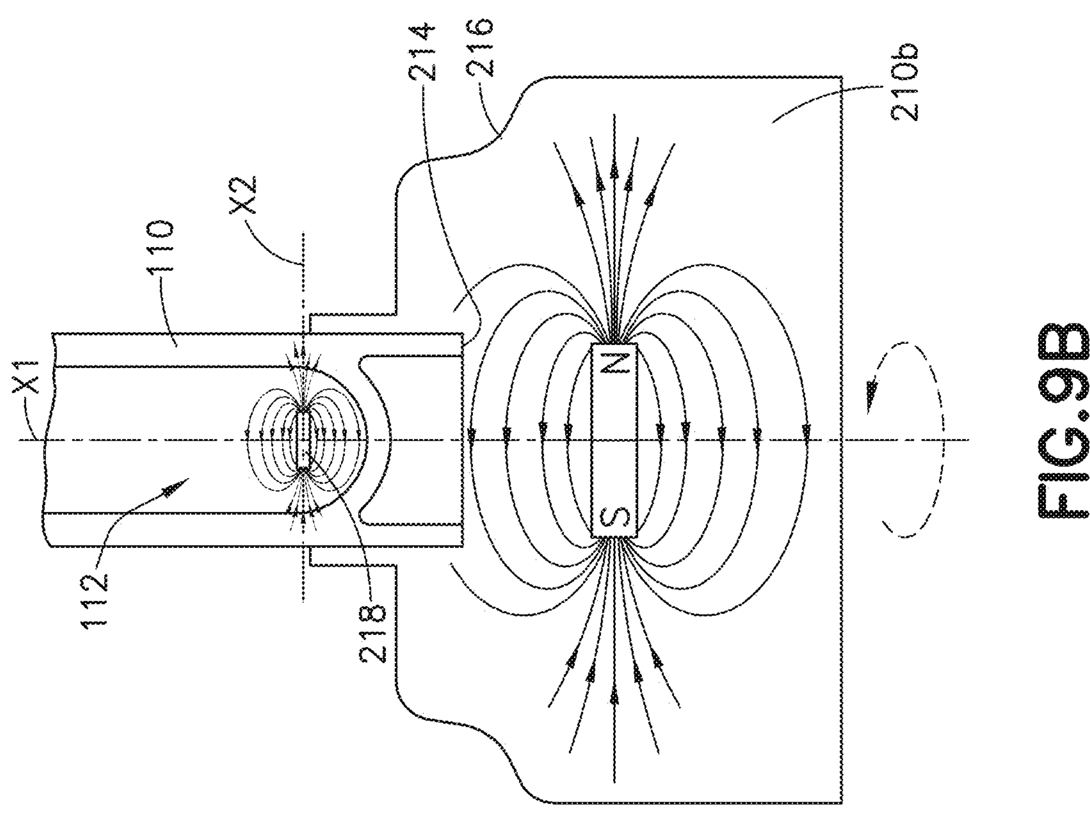
FIG. 9B is a schematic drawing of a cross-sectional view of the sample collection container and magnetic stirrer of FIG. 9A.
Figure 9A:
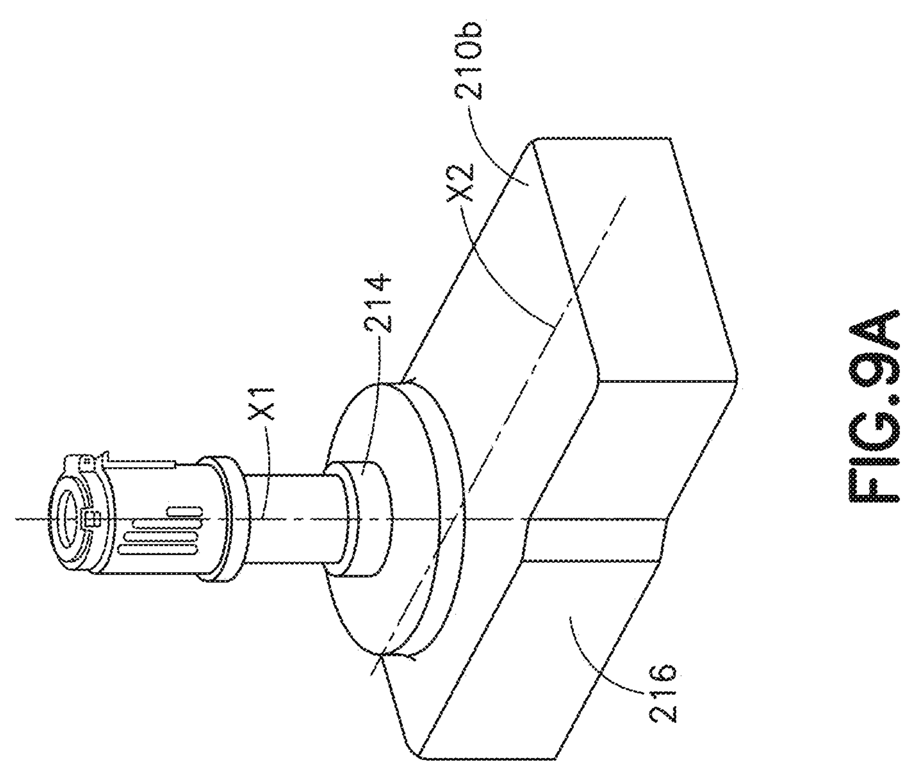
FIG. 9A is a perspective view of a sample collection container and magnetic stirrer, according to an aspect of the present disclosure.

With reference to FIGS. 9A-10B, in other examples, the sample collection container 16 is inserted into a receptacle 214 of a mixing machine 210*b* that uses a magnetically driven stirring action to create the turbulent flow in the container 112. For example, as shown in FIGS. 9A-10B, a magnetic stirrer rod 218 is placed in the container cavity 112. The stirrer rod 218 is configured to rotate or spin when exposed to magnetic forces generated by the magnetic stirrer machine 210*b*. The orientation of the sample collection container 16 relative to the mixing machine 210*b* determines the direction of rotation of the stirrer rod 218. Specifically, as shown in FIGS. 9A and 9B, the mixing machine 210*b* is in an upright orientation with the sample collection container 16 inserted into a receptacle 214 of the machine 210*b*, such that an axis X1 of the sample collection container 16 is transverse or substantially transverse to an axis X2 of the machine 210*b*. As shown in FIG. 9B, when the machine 210*b* is activated, a magnetic field is created. The magnetic field causes the magnetic stirrer rod 218 to rotate about the axis X1 of the sample collection container 16.

Figures 10A, 10B:
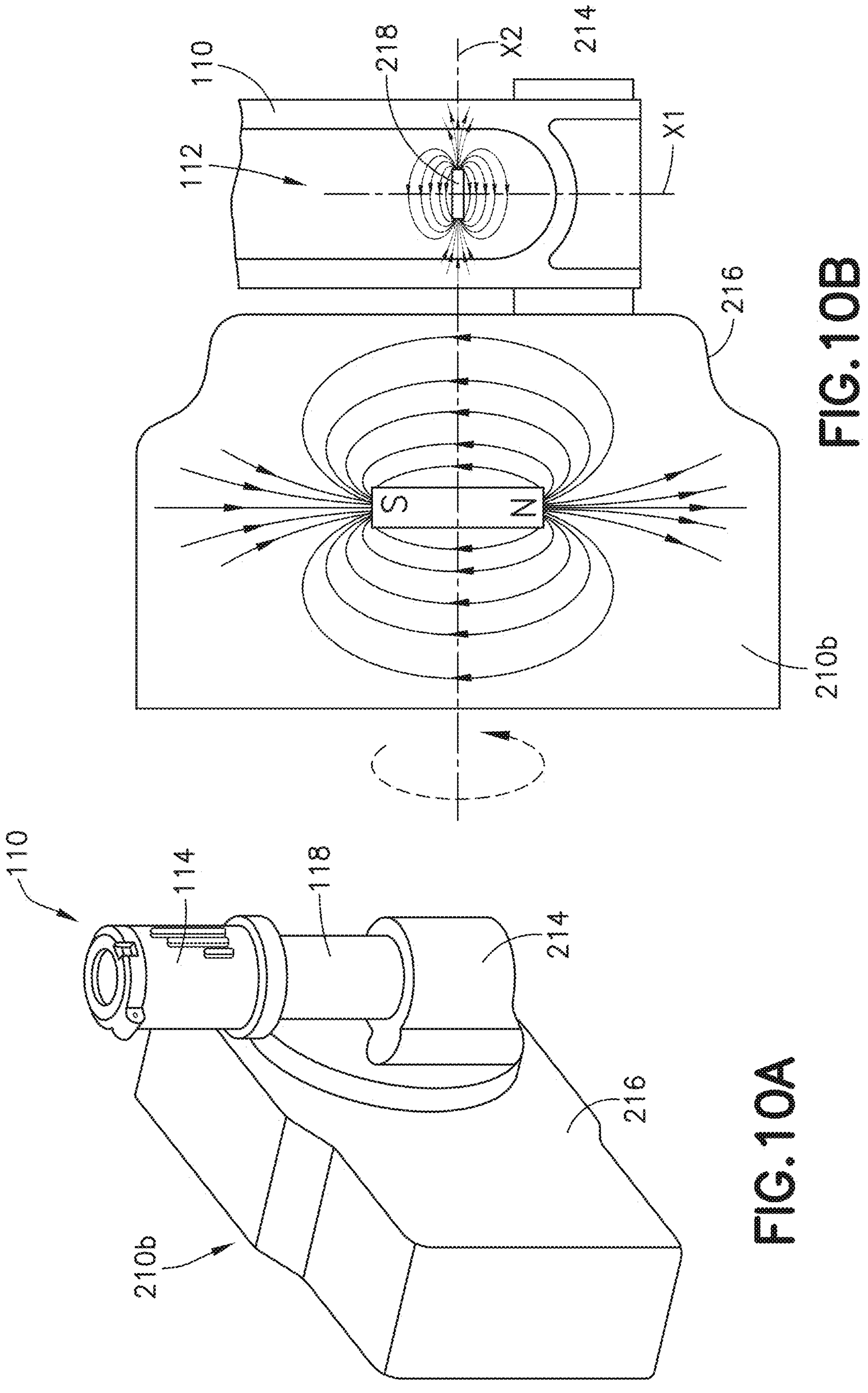
FIG. 10A is a perspective view of a sample collection container and magnetic stirrer in a second (i.e., sideways) orientation, according to an aspect of the present disclosure.
FIG. 10B is a schematic drawing of a cross-sectional view of the sample collection container and magnetic stirrer of FIG. 10A.

In FIGS. 10A and 10B, the mixing machine 210*b* is in a reverse orientation, in which the mixing machine 210*b* rests on its side. The sample collection container 16 is inserted into the receptacle 214 oriented to hold the sample collection container 16 such that the axis X1 of the sample collection container 16 is skew to (i.e., does not intersect) the axis X2 of the machine 210*b*. Instead, the axis X1 of the sample collection container 16 is spaced apart from the axis X2 of the mixing machine 210*b*. As shown in FIG. 10B, when the mixing machine 210*b* is activated, the generated electromagnetic field causes the stirrer rod 218 in the container 16 to rotate about an axis X3 that is transverse or substantially transverse to the axis X1 of the sample collection container 16.

Figure 11B:
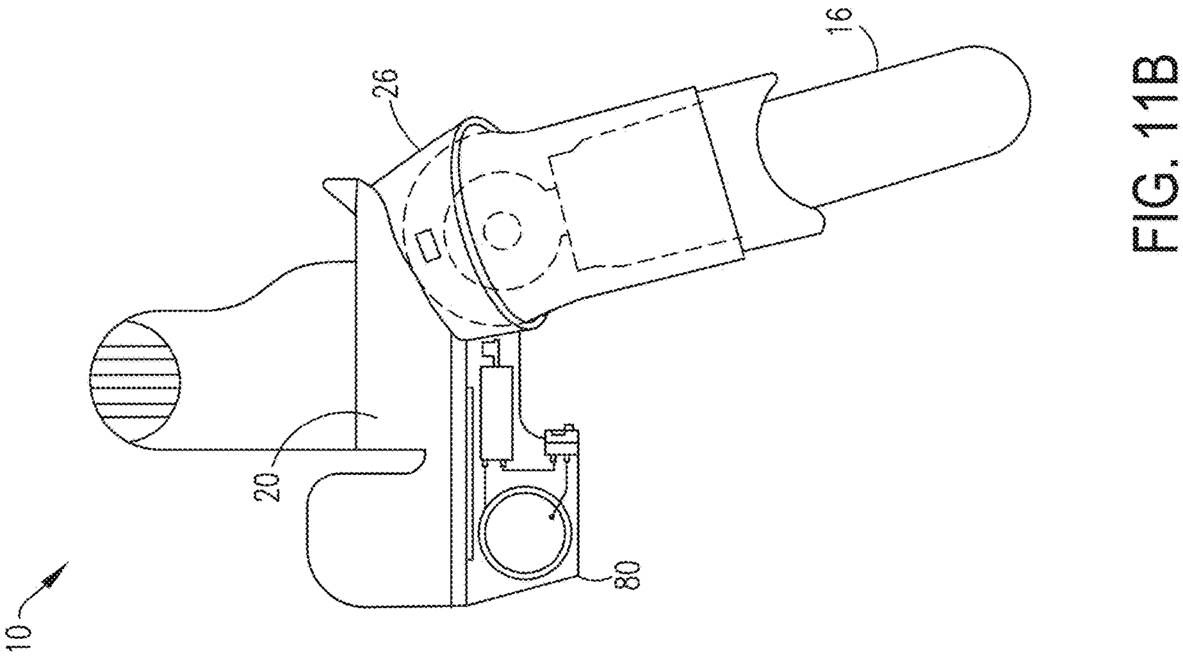
FIGS. 11A and 11B are side views of an assembly including a blood collection device, electronic vibrating device, and sample collection container, according to aspects of the present disclosure.
Figure 11A:
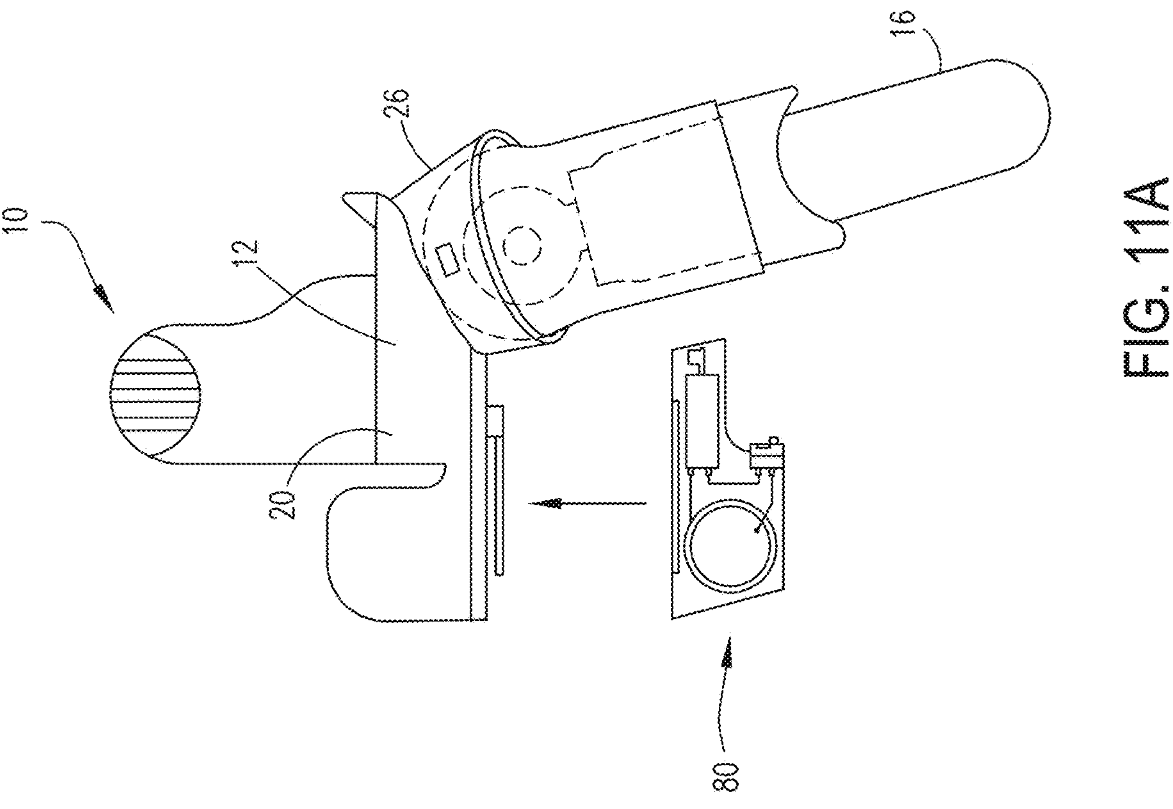

In some examples, as shown in FIGS. 11A and 11B, the blood collection device 10 can include components that attach to the blood collection device 10 and/or sample collection container 16 to create turbulent flow in a collected blood sample without needing to use external or stand-alone devices, such as the previously described mixing machines 210*a*, 210*b*. For example, as shown in FIGS. 11A and 11B, an electronic device 80, such as an electromechanical vibrator, can attach to the finger receiving portion 20 of the blood collection device 10. When the electronic device 80 is activated, the entire blood collection device 10 including the sample collection container 16 attached to the port 26 of the finger receiving portion 20 can be made to vibrate, thereby creating turbulent flow in the sample collection container 16. An exemplary vibration module that can be attached to a blood collection device, and which can be adapted for use with the sample collection containers of the present disclosure, is described in U.S. Patent Appl. Pub. No. 2021/0196164, entitled "Blood Collection Assembly with Vibration Module," which is incorporated by reference in its entirety.

In other examples, the electronic device 80 attached to the finger receiving portion 20 of the blood collection device 10 can be a magnetic stirrer device that generates a magnetic field. As in the examples of FIGS. 9A-10B, when the magnetic field generator is activated, a magnetic stirrer rod 218 (shown in FIGS. 9A-10B) in the sample collection container 16 spins or rotates about a central axis of the container 16, about an axis transverse to the central axis of the container body, or in any other desired orientation. The spinning or rotating rod 218 mixes the sample, thereby ensuring that the additive composition is well distributed through the container 16.

Sample Collection Containers for Reverse Centrifugation

In some examples, the sample collection containers 16 can be configured for reverse centrifugation with the sample collection container 16 inserted into the mixing machine, such as the centrifuge 210*a* or vortex machine, in a reverse orientation. During "reverse centrifugation" the sample collection container 16 is inverted, such that the serum/plasma is separated from whole blood in the upper portion 114 or cap side of the container body 110. The cells and the gel remain in the cap or upper portion 114 following centrifugation. The separated serum can collect in the lower portion 118 of the container body 112.

Figure 12A:
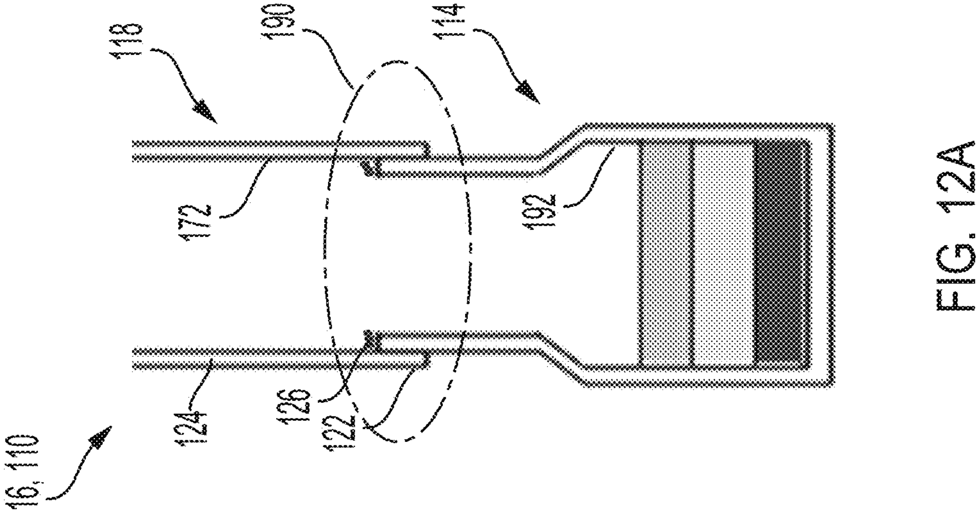
FIG. 12A is a schematic drawing of a cross-sectional view of a container body with an upper portion or cap inserted into a lower portion, according to an aspect of the present disclosure.

In order to provide a high quality blood sample by reverse centrifugation, the present inventors have recognized that the sample collection container 16 should be modified from a standard sample collection container as follows. First, it may be necessary to optimize the geometry of the interface between the lower portion 118 and the upper portion 114 or cap of the container body 110 to ensure that cells are not damaged by sharp edges or protruding surfaces at the interface between portions 114, 118 of the body, which can be referred to as cell hang-up. An example of an interface 190 between the lower portion 118 and the upper portion 114 or cap of a container body 110 of a sample collection container 16 used for standard upright centrifugation is shown in FIG. 12A. As shown in FIG. 12A, the upper portion 114 or cap is inserted into the open top 122 of the lower portion 118. In this arrangement, the lower edge or bottom 126 of the upper portion 114 or cap forms an annular shelf, encircled by reference number 190 in FIG. 12A. It is believed that blood cells may collect or hang up on the annular edge or shelf damaging the cells, thereby increasing an amount of cell hemolysis in the blood sample.

Figure 12B:
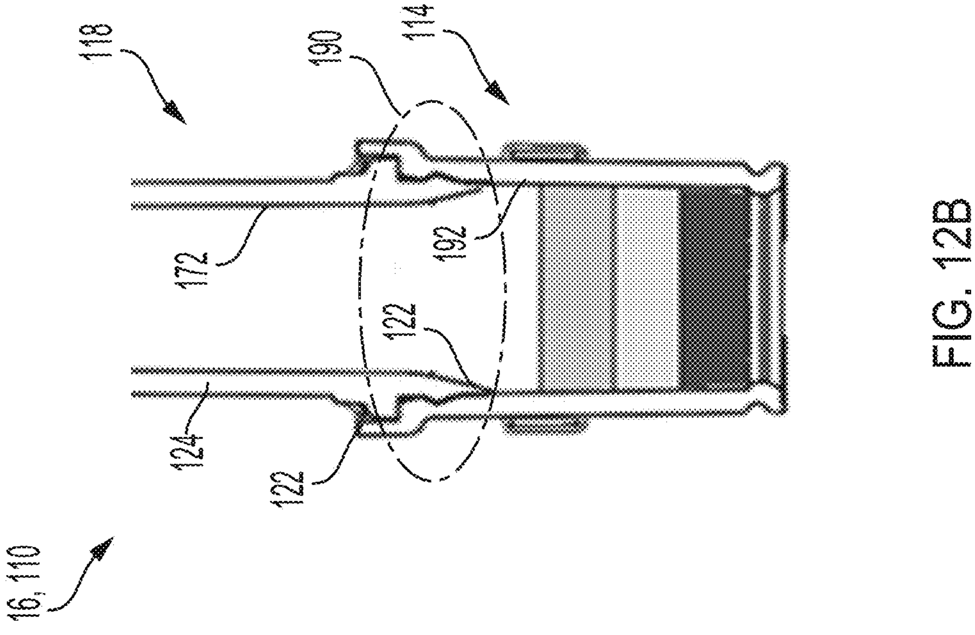
FIG. 12B is a schematic drawing of a cross-sectional view of a lower portion of a container body inserted into an upper portion or cap and including a tapered interface between the upper portion and the lower portion, according to an aspect of the present disclosure.

In contrast, the container 16 shown in FIG. 12B is optimized for reverse centrifugation. As shown in FIG. 12B, the upper portion 114 or cap is inserted over the open top 122 of the lower portion 118 of the container body 110. Further, the inner surface 172 of the interior wall 124 proximate to the open top 122 of the lower portion 118 is tapered creating a smooth or flush transition between the inner surface 172 of the lower portion 118 and the inner surface 192 of the upper portion 114 or cap of the container body 112. Further, the interface 190 between the inner surface 172 of the interior wall 124 of the lower portion 118 and the inner surface 192 of the upper portion 114 or cap is free from protrusions.

The present inventors have recognized that providing this smooth or flush transition between the lower portion 118 and the upper portion 114 or cap improves transfer or movement of cellular particles through the container cavity 112 during centrifugation. Improving this movement or transfer for cellular materials reduces hemolysis and improves a quality of the collected blood sample.

Figure 13B:
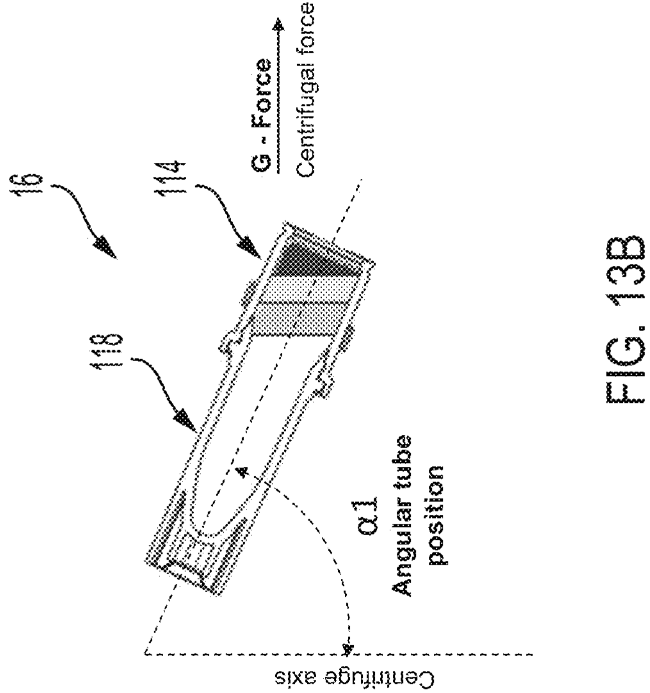
FIG. 13B is a schematic drawing showing layers of cells, serum, and gel in a sample collection container after centrifuging in an angled orientation, according to an aspect of the present disclosure.
Figure 13A:
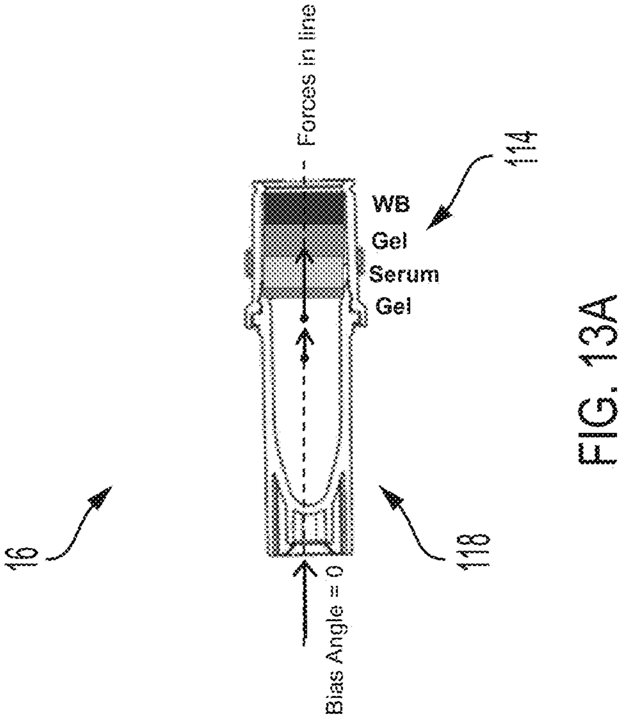
FIG. 13A is a schematic drawing showing layers of cells, serum, and gel in a sample collection container after centrifuging in an upright orientation, according to an aspect of the present disclosure.

The present inventors have also recognized that a centrifugation angle $\alpha$1 (i.e., an angle of the sample collection container relative to vertical) can be an important parameter for ensuring that a suitable blood sample is obtained. FIGS. 13A and 13B are schematic drawings showing a sample collection container 16 and blood sample following centrifugation. As will be appreciated by those skilled in the art, centrifugation causes the blood sample to separate into a serum layer, a blood cell layer, and one or more gel layers. As shown in FIG. 13A, reverse centrifugation of an upright sample collection container 16 (i.e., when the upper portion 114 or cap is inserted into a receptacle of the centrifugation machine in an upright orientation, with an angle $\alpha 1$ of 0 degrees, as shown in FIG. 8A) produces a serum layer between two gel layers.

FIG. 13B shows a sample collection container 16 centrifuged by reverse centrifugation at an angle $\alpha 1$ about 75 degrees. As shown in FIG. 13B, the gel layer is between the cell layer and the serum layer. There is no gel layer on top of the serum, as was the case for the upright container 16, shown in FIG. 13A.

Figure 13C:
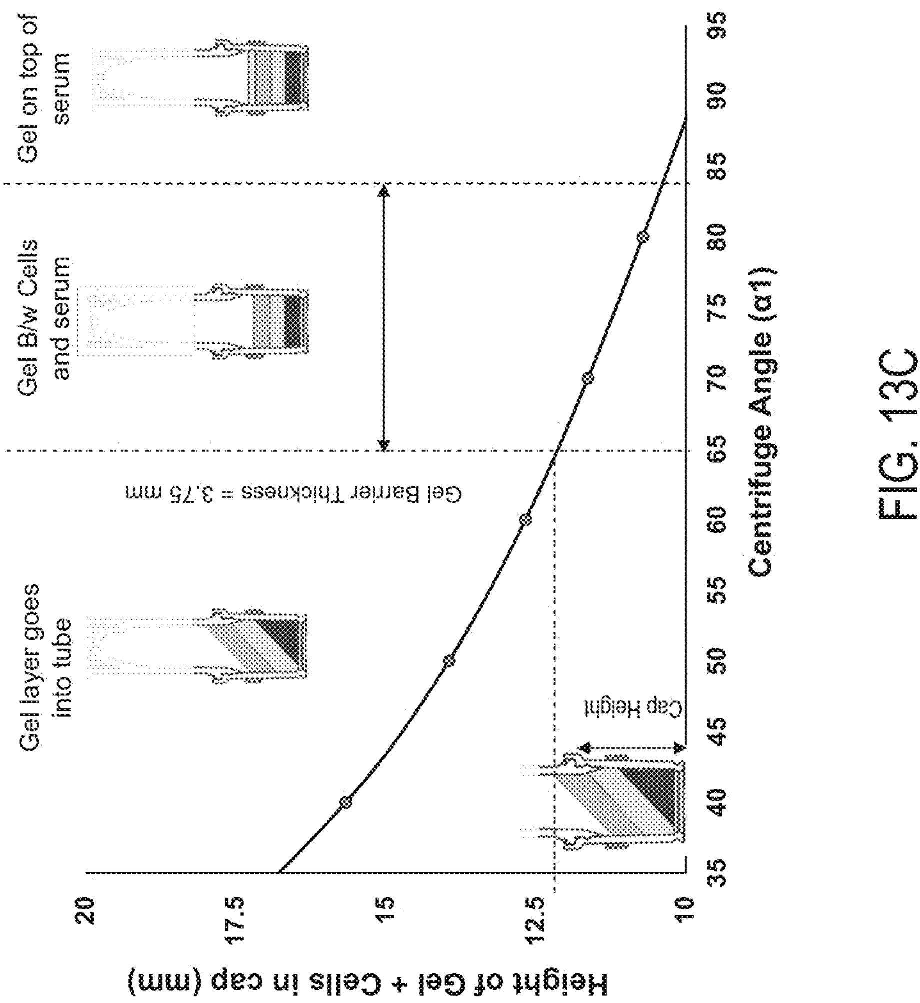
FIG. 13C is a graph showing a relationship between height of gel and cells in a centrifuged sample (by reverse centrifugation) and centrifuge angle, according to an aspect of the present disclosure.

FIG. 13C is a graph showing the relationship between the centrifugation angle $\alpha 1$ and the height of the gel layer and the cell layer in the upper portion 114 or cap of a sample collection container 16 following reverse centrifugation. As shown in FIG. 13C, the height of the cells and gel layers decreases as the centrifugation angle $\alpha 1$ increases. Based on the measurements shown in FIG. 13C, the present inventors have determined that the centrifugation angle $\alpha 1$ should be between about 65 degrees and about 85 degrees in order for proper sample separation to occur (i.e., to form a clean separation barrier between the cells and the serum). It has been determined that if the angle $\alpha 1$ is greater than about 85 degrees, there is risk of formation of gel on top of the separated serum, which is shown schematically in FIG. 13A. Conversely, if the angle $\alpha 1$ is less than about 65 degrees, the gel barrier may go across the interface 190 (shown in FIG. 13B) between the lower portion 118 and the upper portion 114 or cap of the container body 110, which will impact the removal of the upper portion 114 to access the blood sample. In contrast, the arrangement of layers shown in FIG. 13B, where the gel layer does not go across the interface 190 between the lower portion 118 and the upper portion 114 or cap of the container body 112 is preferred.

Sample Collection Container and Lubricant

In some examples, the present inventors have recognized that it may be necessary to provide a hydrophobic coating at the interface 190 between the lower portion 118 and the upper portion 114 or cap of the container body 110. For example, the coating can be a lubricant or surfactant that creates a hydrophobic barrier to blood, thereby reducing cell hang up at the interface 190 between the lower portion 118 and the upper portion 114 or cap. As previously described, reducing cell hang up preserves cells which contributes to improved blood sample quality. In some examples, the lubricant can be a biocompatible lubricant that does not interact with and which is not absorbed by blood cells, such as silicone fluid (e.g., polydimethylsiloxane). The amount of lubricant at the interface 190 needed to provide a good quality blood sample will be determined by those skilled in the art based upon the size, shape, and geometry of the interface 190 and container body 110. In order to ensure good sample quality, in some examples, at least about 0.5 mg of lubricant, or, preferably, from about 0.5 mg of the lubricant to about 2.0 mg of the lubricant is provided at the interface 190.

Figure 14:
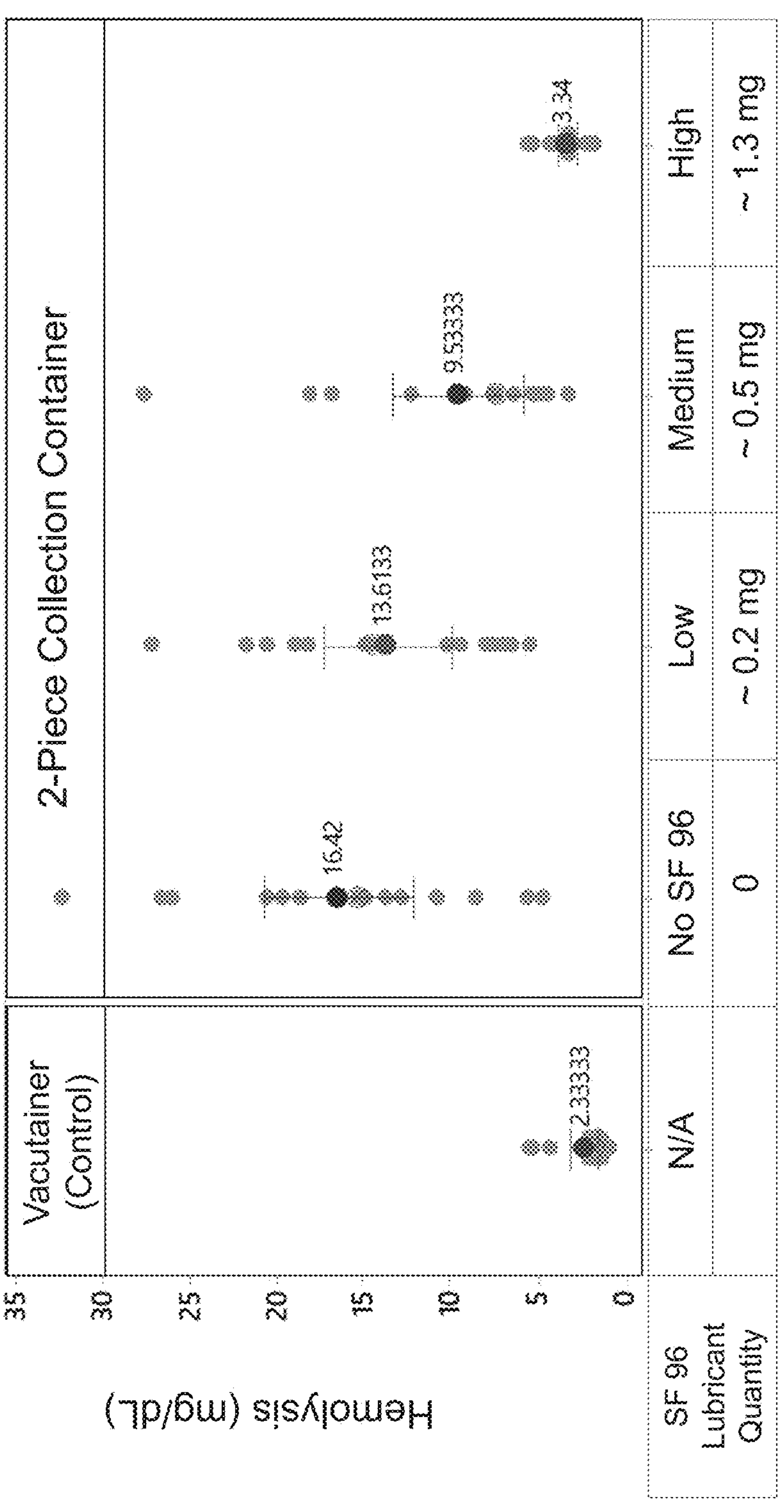
FIG. 14 is a graph showing effects of using a lubricant on an interface between upper and lower portions of a two-piece sample collection container, according to an aspect of the present disclosure.

FIG. 14 is a graph showing effects of providing a lubricant at the interface 190 between the lower portion 118 and upper portion 114 or cap of the sample collection container 16. As shown in FIG. 14, for a vacutainer tube (i.e., a single-piece tube without an interface), the amount of hemolysis in a blood sample was very low (2.33 mg/dL). However, when a two-piece sample collection container, such as any of the sample collection containers 16 disclosed herein having an interface 190 between a lower portion 118 and an upper portion 114 or cap of the container body 112 is used, the amount of hemolysis increases. Specifically, when a blood sample in the two-piece sample collection container without any lubricant is centrifuged by reverse centrifugation, the amount of hemolysis increases to 16.42 mg/dL. When lubricant is applied to the interface 190 between the lower portion 118 and the upper portion 114 or cap, the amount of hemolysis decreases. In particular, when a high amount of SF 96 lubricant (about 1.3 mg of lubricant) is applied to the interface 190, the amount of hemolysis is 3.34 mg/dL. Accordingly, it can be appreciated that a lubricant in the quantities of from 0.5-5 mg/dL helps with minimizing any cell hang up and hemolysis level post reverse centrifugation.

While different examples of the sample collection containers and blood collection devices of the present disclosure are shown in the accompanying figures and described hereinabove in detail, other examples will be apparent to, and readily made by, those skilled in the art without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A sample collection container configured to be removably mounted to a blood collection device, the sample collection container comprising:

a housing comprising a first end, a second end, a flow channel having an inlet and an outlet extending at least partially between the first end and the second end of the housing;

a container body removably connected to the second end of the housing comprising an open top, a closed bottom, and an interior wall extending between the top and the bottom, which define a collection cavity, wherein, when the housing is connected to the container body, the outlet of the flow channel is in fluid communication with the collection cavity; and at least one additive dispersing object configured to be positioned to be contacted by blood flowing from the blood collection device through the flow channel or into the collection cavity, the at least one additive dispersing object comprising an additive composition configured to be mixed with the blood passing along the flow channel and into the collection cavity, wherein the at least one additive dispersing object comprises:

a disk sized to fit within the collection cavity of the container body to stabilize the at least one additive dispersing object within the container cavity in an upright orientation; and at least one post extending from either an upper surface or a lower surface of the disk.

2. The sample collection container of claim 1, wherein the housing further comprises at least one flow directing protrusion adjacent the inlet for directing blood from the blood collection device into the flow channel.

3. The sample collection container of claim 2, wherein the at least one flow directing protrusion is configured to provide a fluid attachment point for blood to attach to, thereby controlling the flow of blood from a skin surface of a patient's finger to the flow channel of the housing.

4. The sample collection container of claim 2, wherein the at least one flow directing protrusion comprises an attachment pillar.

5. The sample collection container of claim 1, wherein the bottom of the container body comprises a sloped bottom that slopes towards a portion of the interior wall of the container body forming a depression sized to receive the at least one additive dispersing object.

6. The sample collection container of claim 5, wherein, when the at least one additive dispersing object is received in the depression, the at least one additive dispersing object does not interfere with a probe inserted into the container cavity through the open top of the container body.

7. The sample collection container of claim 1, wherein the additive composition comprises a sample stabilizing composition and/or a composition that preserves a specific element of blood, such as RNA or a protein analyte.

8. The sample collection container of claim 1, wherein the additive composition comprises a dry anticoagulant, such as Heparin or Ethylenediaminetetraacetic acid (EDTA).

9. The sample collection container of claim 1, wherein the at least one additive dispersing object comprises an open cell foam or a closed cell foam that is impregnated with the additive composition.

10. The sample collection container of claim 1, wherein the at least one additive dispersing object comprises an open cell foam comprising at least one of melamine or formaldehyde-melamine-sodium bisulfite copolymer.

11. The sample collection container of claim 1, wherein the at least one additive dispersing object is disposed proximate to the inlet of the flow channel of the housing.

12. The sample collection container of claim 1, wherein the at least one additive dispersing object comprises an elongated pillar configured to be mounted over the at least one directing protrusion.

13. The sample collection container of claim 1, wherein the at least one additive dispersing object is adhered to an inner surface of the interior wall of the container body.

14. The sample collection container of claim 1, wherein the at least one additive dispersing object comprises a hollow, tubular foam structure formed by an extrusion process.

15. The sample collection container of claim 1, wherein the at least one additive dispersing object comprises a molded part comprising an exterior surface coated by the additive composition.

16. The sample collection container of claim 15, wherein the molded part comprises:

the disk and the disk is sized to fit within the collection cavity of the container body to stabilize the molded part within the container cavity in an upright orientation; and the at least one post extending from either an upper surface or a lower surface of the disk.

17. The sample collection container of claim 1, wherein, in the upright orientation, a longitudinal axis of the at least one post is parallel to a longitudinal axis of the container body.

18. The sample collection container of claim 16, wherein the at least one post comprises a plurality of lower posts extending downwardly from a lower surface of the disk, and wherein the plurality of lower posts comprise radially inwardly angled free ends.

19. The sample collection container of claim 18, further comprising a ball at least partially retained by the inwardly angled free ends of the lower posts configured to move through the container cavity to agitate blood in the container cavity.

20. The sample collection container of claim 1, further comprising an agitation member, such as a buoyant or heavy ball, disposed in the container cavity and configured to move through the container cavity to agitate blood in the container cavity.

21. The sample collection container of claim 1, further comprising an agitation tool positioned in the collection cavity proximate to the outlet of the flow channel for agitating blood as it is expelled from the flow channel into the container cavity.

22. The sample collection container of claim 21, wherein the agitation tool comprises a fin or blade extending about a post positioned such that the blood expelled from the flow channel contacts the fin or blade causing the fin or blade to rotate about the post, thereby agitating the blood and mixing the blood with the additive composition.

23. A blood collection assembly comprising:

a finger holder comprising a finger receiving portion and an actuation portion; and a sample collection container configured to be removably mounted to the finger holder, the sample collection container comprising:

a housing comprising a first end removably connectable to the finger holder, a second end, a flow channel having an inlet and an outlet extending at least partially between the first end and the second end of the housing, and at least one flow directing protrusion adjacent the inlet for directing blood from the blood collection device into the flow channel;

a container body removably connected to the second end of the housing comprising an open top, a lower portion comprising a closed bottom, and an interior wall extending between the top and the bottom, which define a collection cavity, wherein, when the housing is connected to the container body, the outlet of the flow channel is in fluid communication with the collection cavity; and at least one additive dispersing object configured to be positioned to be contacted by blood flowing from the blood collection assembly through the flow channel or into the collection cavity, the at least one additive dispersing object comprising an additive composition configured to be mixed with the blood passing along the flow channel and into the collection cavity, wherein the at least one additive dispersing object comprises:

a disk sized to fit within the collection cavity of the container body to stabilize the at least one additive dispersing object within the container cavity in an upright orientation; and at least one post extending from either an upper surface or a lower surface of the disk.

24. The blood collection assembly of claim 23, wherein the additive composition comprises a sample stabilizing composition and/or a composition that preserves a specific element of blood, such as RNA or a protein analyte.

25. The blood collection assembly of claim 23, wherein the additive composition comprises a dry anticoagulant, such as Heparin or Ethylenediaminetetraacetic acid (EDTA).

26. The blood collection assembly of claim 23, wherein the at least one additive dispersing object comprises an open cell foam or a closed cell foam that is impregnated with the additive composition.

27. The blood collection assembly of claim 23, wherein the at least one additive dispersing object comprises an open cell foam comprising at least one of melamine or formaldehyde-melamine-sodium bisulfite copolymer.

28. The blood collection assembly of claim 23, further comprising an electronic vibrator mounted to the finger holder that, when activated, agitates a fluid sample contained in the sample collection container.

29. The blood collection assembly of claim 23, further comprising a magnetic stirrer mounted to the finger holder that, when activated, causes a magnetic stirrer rod in the sample collection container to spin, thereby agitating a blood sample in the sample collection container.

* * * * *